(12) United States Patent
Xu et al.

(10) Patent No.: US 11,377,654 B2
(45) Date of Patent: Jul. 5, 2022

(54) APPLICATION OF IMMOBILIZED ENZYMES FOR NANOPORE LIBRARY CONSTRUCTION

(71) Applicant: New England Biolabs, Inc., Ipswich, MA (US)

(72) Inventors: Ming-Qun Xu, Hamilton, MA (US); Yi Fang, Topsfield, MA (US); Aihua Zhang, Hamilton, MA (US); Luo Sun, Hamilton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 83 days.

(21) Appl. No.: 17/018,862

(22) Filed: Sep. 11, 2020

(65) Prior Publication Data
US 2022/0090056 A1    Mar. 24, 2022

(51) Int. Cl.
*C12N 15/10* (2006.01)
*C12Q 1/6806* (2018.01)
*C12Q 1/6869* (2018.01)

(52) U.S. Cl.
CPC ....... *C12N 15/1065* (2013.01); *C12Q 1/6806* (2013.01); *C12Q 1/6869* (2013.01)

(58) Field of Classification Search
CPC . C12N 15/1065; C12Q 1/6806; C12Q 1/6869
See application file for complete search history.

(56) References Cited

U.S. PATENT DOCUMENTS

| | | | |
|---|---|---|---|
| 9,657,342 B2 | 5/2017 | Rava et al. |
| 10,633,644 B1 | 4/2020 | Chen et al. |
| 2016/0016140 A1 | 1/2016 | Jovanovich et al. |
| 2018/0142275 A1 | 5/2018 | Roos et al. |

FOREIGN PATENT DOCUMENTS

WO    2019224560 A1    11/2019

OTHER PUBLICATIONS

Fang et al. Catalysts, 9, 732, pp. 1-14; 2019, published Aug. 29, 2019 (Year: 2019).*
Legget et al. Journal of Experimental Botany, vol. 68, No. 20 pp. 5419-5429, 2017 (Year: 2017).*
Keppler, et al., Nature Biotechnology, 21, 86-89, 2003.
Wulf, et al., J. Biol. Chem., 294, 48, 18220-18231, 2019.
Jaworski, et al., PLoS pathogens, 2017. 13(5): p. e1006365.
(Continued)

*Primary Examiner* — Jeremy C Flinders
*Assistant Examiner* — Taryn Kimberly Wood
(74) *Attorney, Agent, or Firm* — New England Biolabs, Inc

(57) ABSTRACT

The present disclosure relates, according to some embodiments, to methods for preparing a library for sequencing. For example, a method may comprise (a) in a coupled reaction, (i) contacting a population of nucleic acid fragments with a tailing enzyme to produce tailed fragments, and (ii) ligating to the tailed fragments a sequencing adapter with a ligase to produce adapter-tagged fragments; and/or separating adapter-tagged fragments from the tailing enzyme and the ligase to produce separated adapter-tagged fragments and, optionally, separated tailing enzyme and/or separated ligase. In some embodiments, a tailing enzyme and/or a ligase used in library preparation may be immobilized enzymes.

15 Claims, 30 Drawing Sheets

Specification includes a Sequence Listing.

(56) References Cited

OTHER PUBLICATIONS

Weirather, et. al., F1000Research, 2017.
Wongsurawat, et al., Frontiers in microbiology, 2019. 10: p. 260.
Zhao, et al., Frontiers in Genetics, 2019. 10: p. 253.
Bruskov, et al., Nucleic Acids Res. 2002. V. 30. p. 1354-1363.
Lindahl, et al., Biochemistry. 1974. V. 13. p. 3405-3410.
Warters, et al., J. Cell Physiol. 1987. V. 133. p. 144-150.
Li, et al, Bioconjugate Chem. 2018, 29, 7, 2316-2324.
Head, et al., BioTechniques 56, 61-64, 66, 68, 2014.
Star, PLOS ONE 9, e89676, 2014.
Mardoum, et al., Front Phys. 2018; 6: 53.
Ojal, et al., European Biophysics Journal, 43, 2-3, 71-79, 2014.
Zhang, et al., Scientific reports, 8.1: 1-11, 2018.
Banin, et al., Clinical Chemistry, 53, 11, 2034-2036 2007.

\* cited by examiner

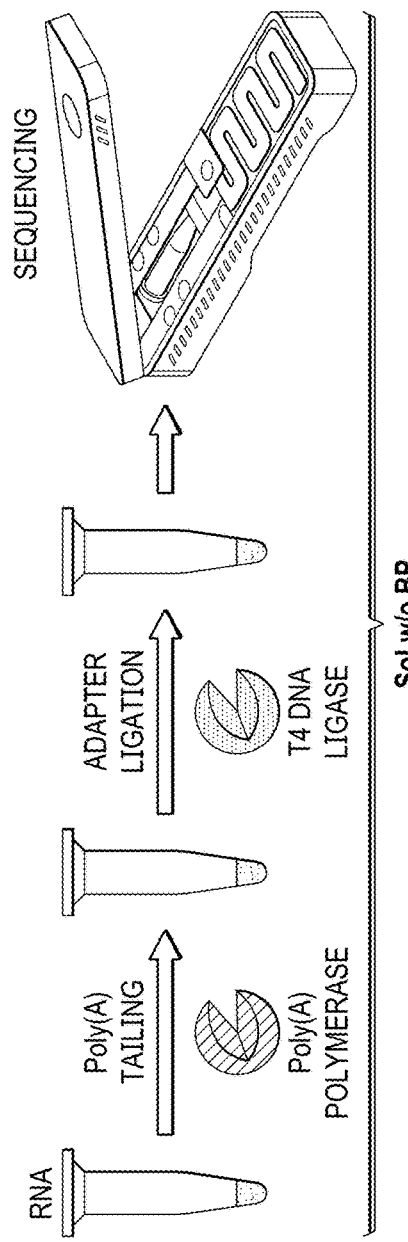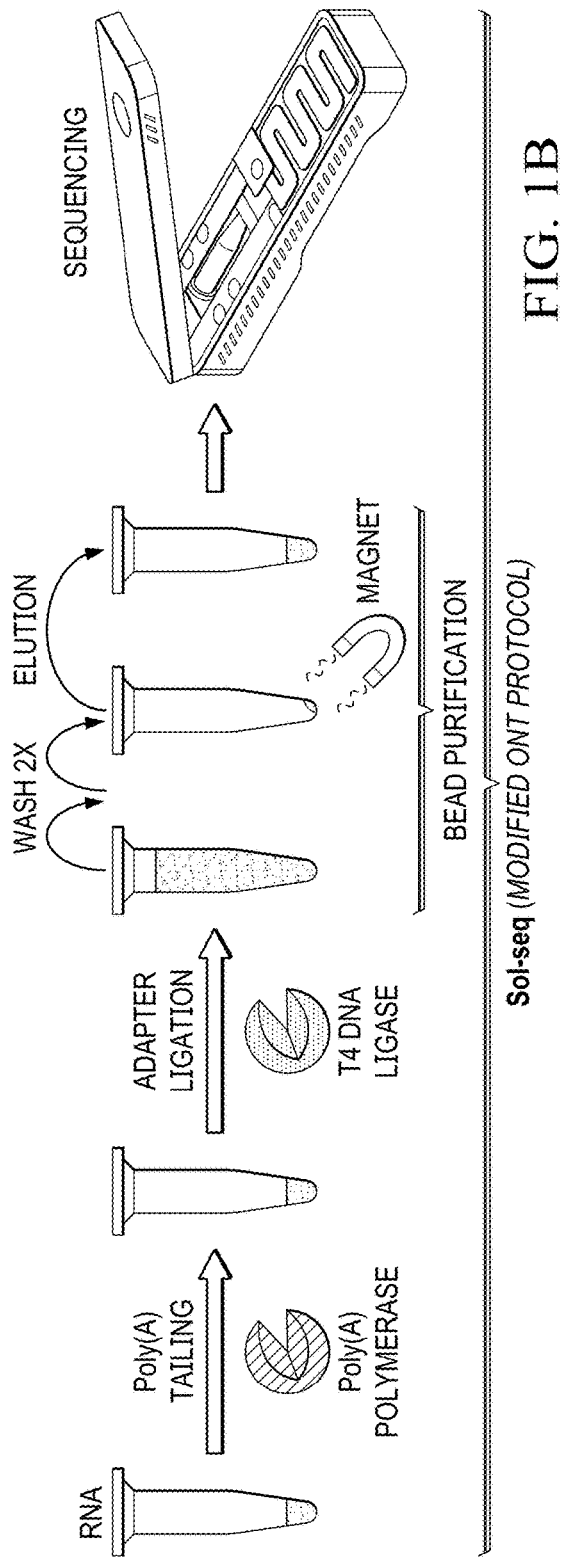

APPLICATION OF IMMOBILIZED ENZYMES FOR NANOPORE LIBRARY CONSTRUCTION

SEQUENCE LISTING STATEMENT

This disclosure includes a Sequence Listing submitted electronically in ascii format under the file name "NEB-424_ST25.txt". This Sequence Listing is incorporated herein in its entirety by this reference.

BACKGROUND

The nanopore sequencing platform provided by Oxford Nanopore Technologies (ONT) is a third-generation sequencing approach to sequence long DNA/RNA molecules through the change of electrical signals as the DNA/RNA passes through the nanopore on a membrane (Jaworski, E. and A. Routh, Parallel ClickSeq® and Nanopore sequencing elucidates the rapid evolution of defective-interfering RNAs in Flock House virus. PLoS pathogens, 2017. 13(5): p. e1006365; Weirather, J. L., et al., Comprehensive comparison of Pacific Biosciences and Oxford Nanopore Technologies and their applications to transcriptome analysis. F1000Research, 2017. 6; Wongsurawat, T., et al., Rapid sequencing of multiple RNA viruses in their native form. Frontiers in microbiology, 2019. 10: p. 260; Zhao, L., et al., Analysis of transcriptome and epitranscriptome in plants using PacBio Iso-Seq® and nanopore-based direct RNA sequencing. Frontiers in Genetics, 2019. 10: p. 253). Nanopore direct RNA sequencing permits generation of full length, strand-specific RNA sequence reads. However, library prep practices with multiple bead purification steps demand relatively high input of RNA or DNA, at least in part, because significant sample loss can occur during these steps. This bead purification procedure may also produce bias in binding and elution of nucleic acid substrates of various lengths so that the output doesn't precisely represent the input library. In particular, polynucleotides (e.g., long or ultralong RNA and DNA templates) may be subjected to breakage and precipitation during bead (e.g., AMPure® bead) purification.

SUMMARY

The present disclosure provides methods for preparing a library for sequencing. For example, a method may comprise (a) in a coupled reaction, (i) contacting a population of nucleic acid fragments with a tailing enzyme to produce tailed fragments, and (ii) ligating to the tailed fragments a sequencing adapter with a ligase to produce adapter-tagged fragments; and/or separating adapter-tagged fragments from the tailing enzyme and the ligase to produce separated adapter-tagged fragments and, optionally, separated tailing enzyme and/or separated ligase. In some embodiments, a tailing enzyme and/or a ligase used in library preparation may be immobilized enzymes. For example, a tailing enzyme may be immobilized on a magnetic bead and/or a ligase may be immobilized on a magnetic bead. Optionally, a tailing enzyme and a ligase may be immobilized on the separate supports or co-immobilized on a single support. A tailing enzyme and/or a ligase, according to some embodiments, may be soluble enzymes. In some embodiments, separating adapter tagged fragments may further comprise subjecting the coupled reaction to a magnetic field (e.g., bringing the sample to a magnet, bringing a magnet to the sample, activating an electromagnetic field). A population of nucleic acid fragments may comprise ribonucleic acid fragments and/or may comprise deoxyribonucleic acid fragments. In some embodiments, methods may be capable of producing sequencing libraries with little input RNA. For example, methods may use a population of nucleic acid fragments having less than 100 ng of nucleic acids or a population of nucleic acid fragments having less than 10 ng of nucleic acids.

The present disclosure further provides methods for preparing sequencing libraries comprise any combination of steps (a) and (b) and further comprise: (c) in a second coupled reaction, (i) contacting a second population of nucleic acid fragments with the separated tailing enzyme to produce additional tailed fragments, and (ii) ligating to the additional tailed fragments a second sequencing adapter with the separated ligase to produce additional adapter-tagged fragments, and/or (d) separating the additional adapter-tagged fragments from the separated tailing enzyme and the separated ligase to produce separated additional adapter-tagged fragments, separated tailing enzyme, and separated ligase. In some embodiments, a method comprise any combination of steps (a), (b), (c), and (d) and may further comprise (e) translocating the separated adapter-tagged fragments through one or more transmembrane pores; (f) detecting electrical changes as the one or more separated adapter-tagged fragments are translocated through the one or more transmembrane pores in an insulating membrane to produce an electrical signal; and/or (g) analyzing the electrical signal to generate a sequence read. In some embodiments, one or more transmembrane pores may retain about 90% of their initial activity after two hours and/or may retain about 50% of their initial activity after 8 hours. One or more transmembrane pores, according to some embodiments of the disclosure, may produce at least 900 sequence reads per transmembrane pore. In some embodiments, a sequencing adapter may be a single-stranded adapter and may comprise a leader sequence; and a first sequence and a second sequence, wherein the first and second sequences are complementary to each other and define a hairpin, wherein the leader sequence is configured to thread into the one or more transmembrane pores.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1A-E schematically illustrates five methods for preparing nucleic acid libraries for sequencing (e.g., Nanopore MinION® sequencing). FIG. 1A shows library construction in two sequential enzymatic steps using soluble enzymes without AMPure® bead purification (Sol without BP). FIG. 1B shows library construction in two sequential enzymatic steps using soluble enzymes with AMPure® bead purification (Sol-seq). FIG. 1C shows library construction in a coupled enzymatic reaction using soluble enzymes with AMPure® bead purification (Sol-cpl). FIG. 1D shows library construction in two sequential enzymatic steps using immobilized enzymes without bead purification (Im-seq). FIG. 1E shows library construction in a coupled enzymatic reaction using immobilized enzymes without bead purification (Im-cpl).

FIG. 16A shows that immobilized poly(A) polymerase, co-immobilized with T4 DNA ligase, is active in a poly(A) tailing assay in which a poly(A) tail is added to a 35-mer RNA (lower panel), but not a corresponding control (upper panel). FIG. 16B shows that immobilized T4 DNA ligase, co-immobilized with poly(A) polymerase on BG-modified beads (BGPL), displayed activity in an adapter ligation assay in which adapters RTA and RMX were ligated to each other (lower panel), but not a control with RTA alone (upper panel).

FIG. 18A shows the number of sequencing reads obtained from 100 ng of *Listeria monocytogenes* RNA libraries prepared using immobilized enzymes following either a sequential reaction method ("Im-seq 100"; Example 4D) or a coupled reaction method ("Im-cpl 100"; Example 4E) without AMPure® bead purification. FIG. 18B shows the number of sequencing reads obtained from 100 ng of mammalian RNA libraries prepared using immobilized ligase ("ImL") or immobilized polymerase and immobilized ligase ("ImP & ImL") without AMPure® bead purification. Each output library was loaded onto Nanopore R9.4.1. flow cells for direct RNA sequencing.

A ligated product can be detected by CE analysis due to the presence of both FAM and ROX probes (as shown in FIG. 18C).

Figure 24A:
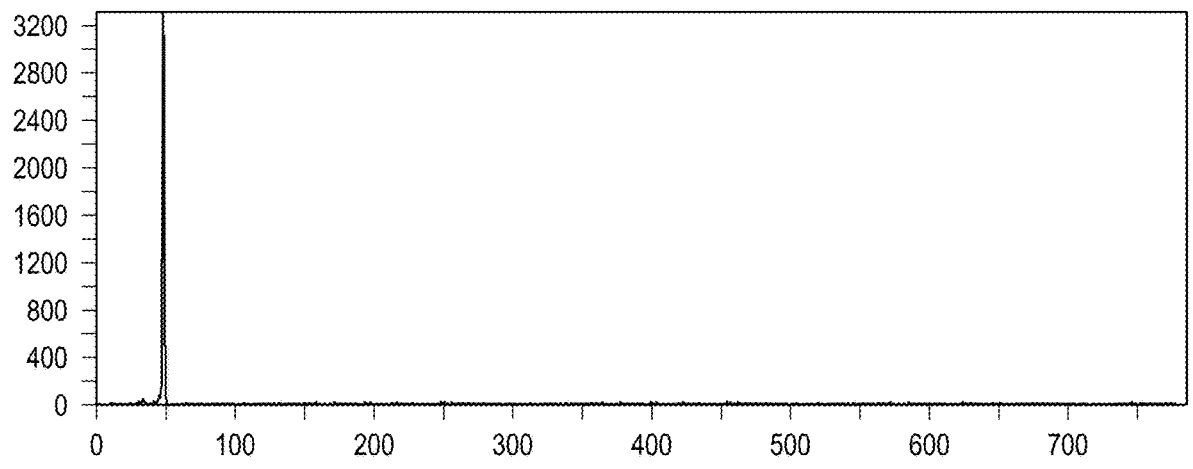
Figure 24A:
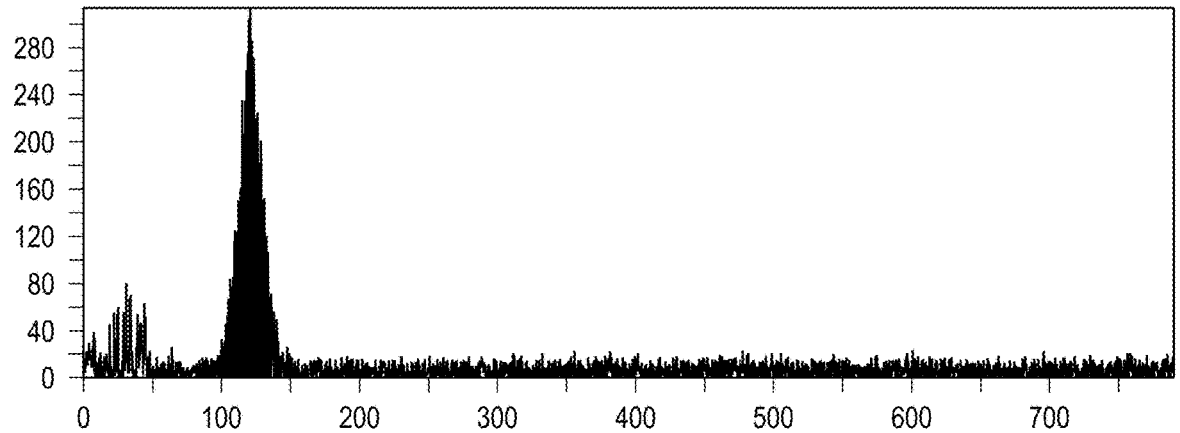
Figure 24A:
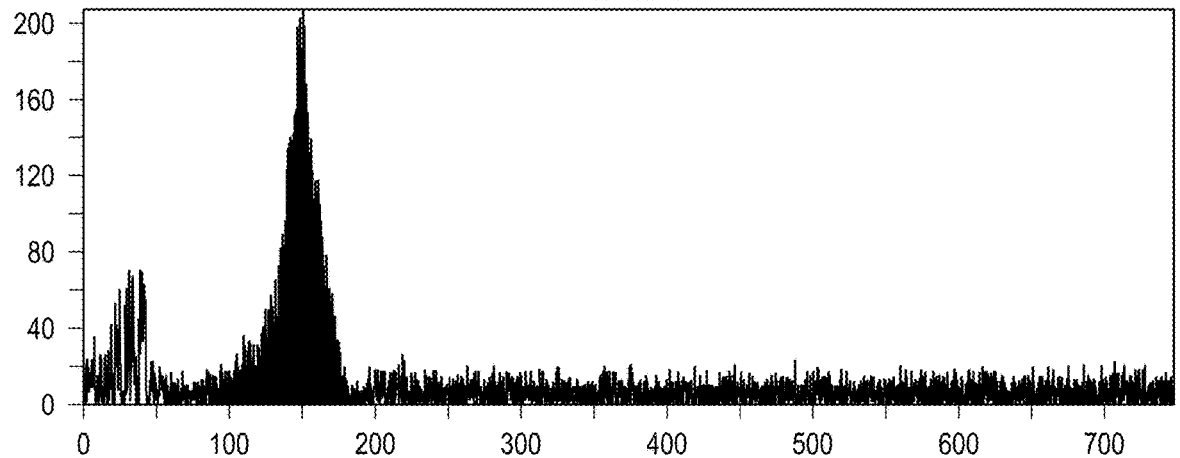
Figure 24B:
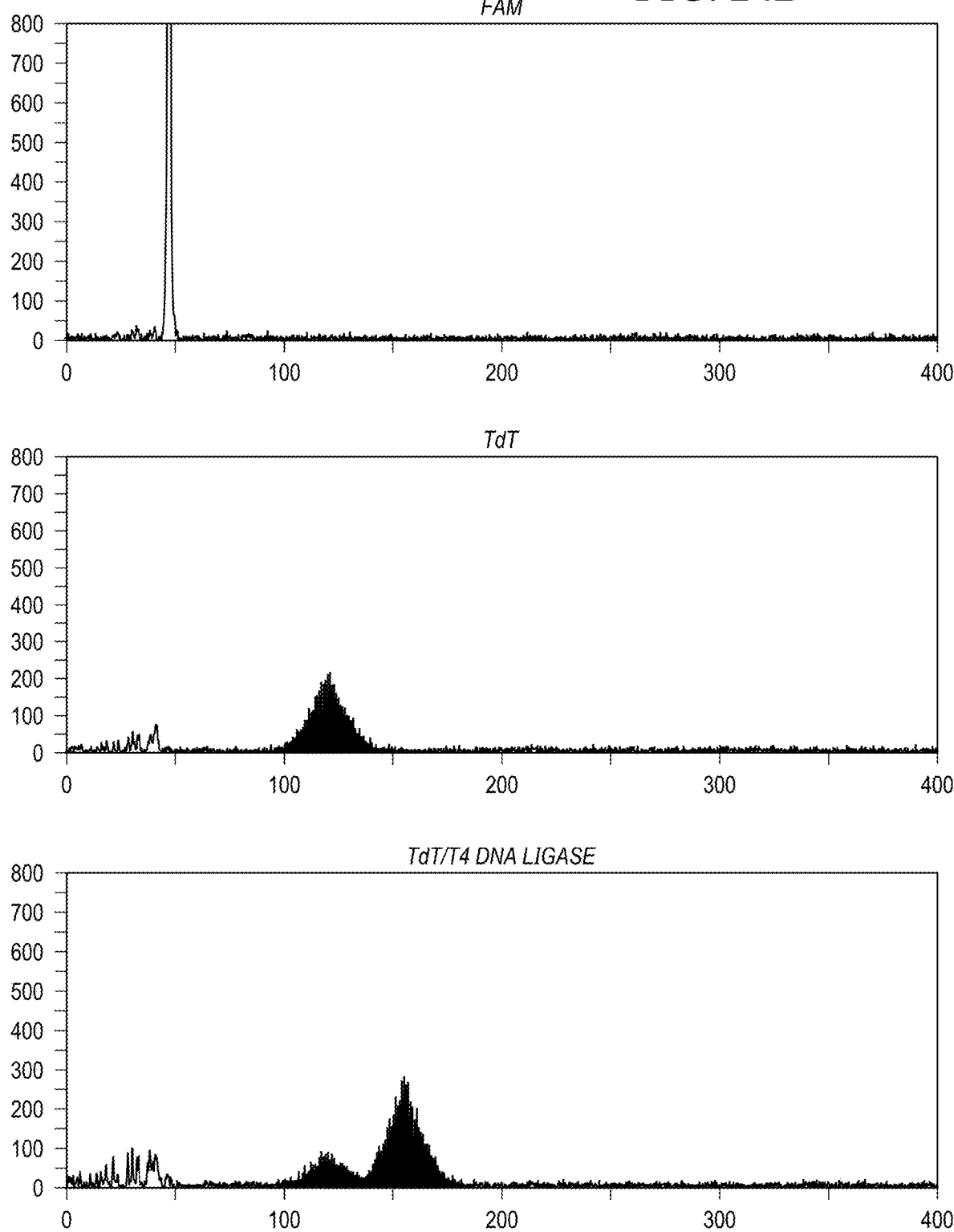
Figure 24C:
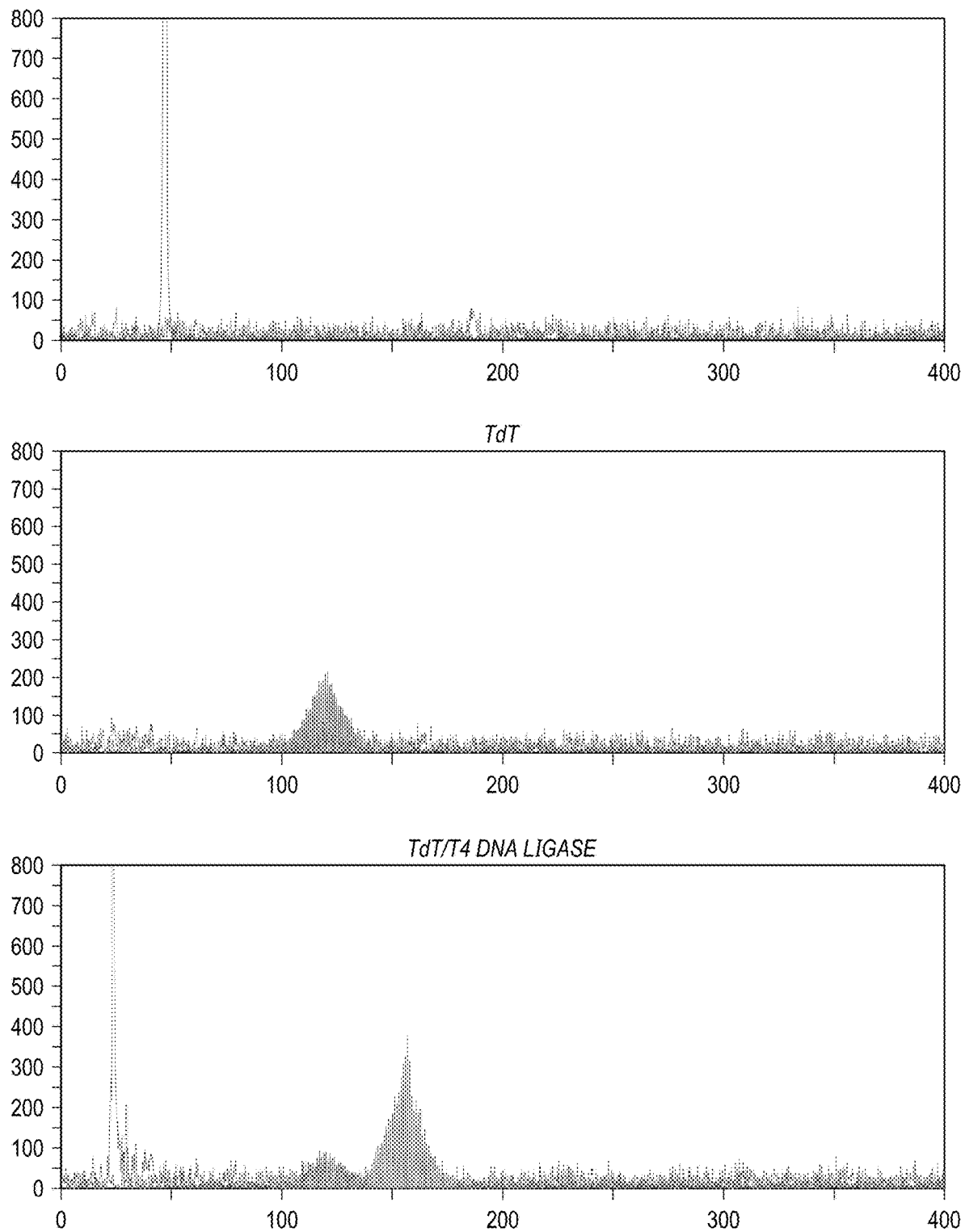

FIG. 24A-C shows sequential poly(dA) and ligation reactions with immobilized enzymes. FIG. 24A shows poly(dA) tailing of 5'FAM-labeled DNA substrate by TdT in two different substrate-to-dATP ratios (1:100 and 1:200). Incorporation of dAMP at the 3' termini of 5'FAM-labeled DNA strand and the length or range of poly(dA) can be detected by CE analysis. FIG. 24B shows detection of a FAM-labeled DNA substrate ligated to ROX-labeled RTA-Poly(dT) using FAM-detecting channel by CE analysis. Top: FAM-labeled DNA substrate; Middle: FAM-labeled DNA substrate treated with TdT shows multiple species corresponding to various poly(dA) length; Bottom: the Poly(dA)-tailed DNA mixture further treated with T4 DNA Ligase in the presence of RTA-Poly(dT) exhibits a shift to a pool of higher molecular mass species with various length of poly(dA) tails. FIG. 24C shows detection of a FAM-labeled DNA substrate ligated to ROX-labeled RTA-Poly(dT) by CE analysis. Top: FAM-labeled DNA substrate without enzyme treatment; Middle: FAM-labeled DNA substrate treated with TdT shows multiple species corresponding to various length of poly(dA) tails; Bottom: detection of the ligation products using both FAM- and ROX-detecting channels (depicted in blue and red, respectively). The Poly(dA)-tailed DNA mixture (as presented in the middle graph) treated with T4 DNA Ligase in the presence of RTA-Poly(dT) exhibits a shift to a pool of higher molecular mass species with various length of poly(dA) tails, with overlapping signals from FAM and ROX probes.

Figure 25:
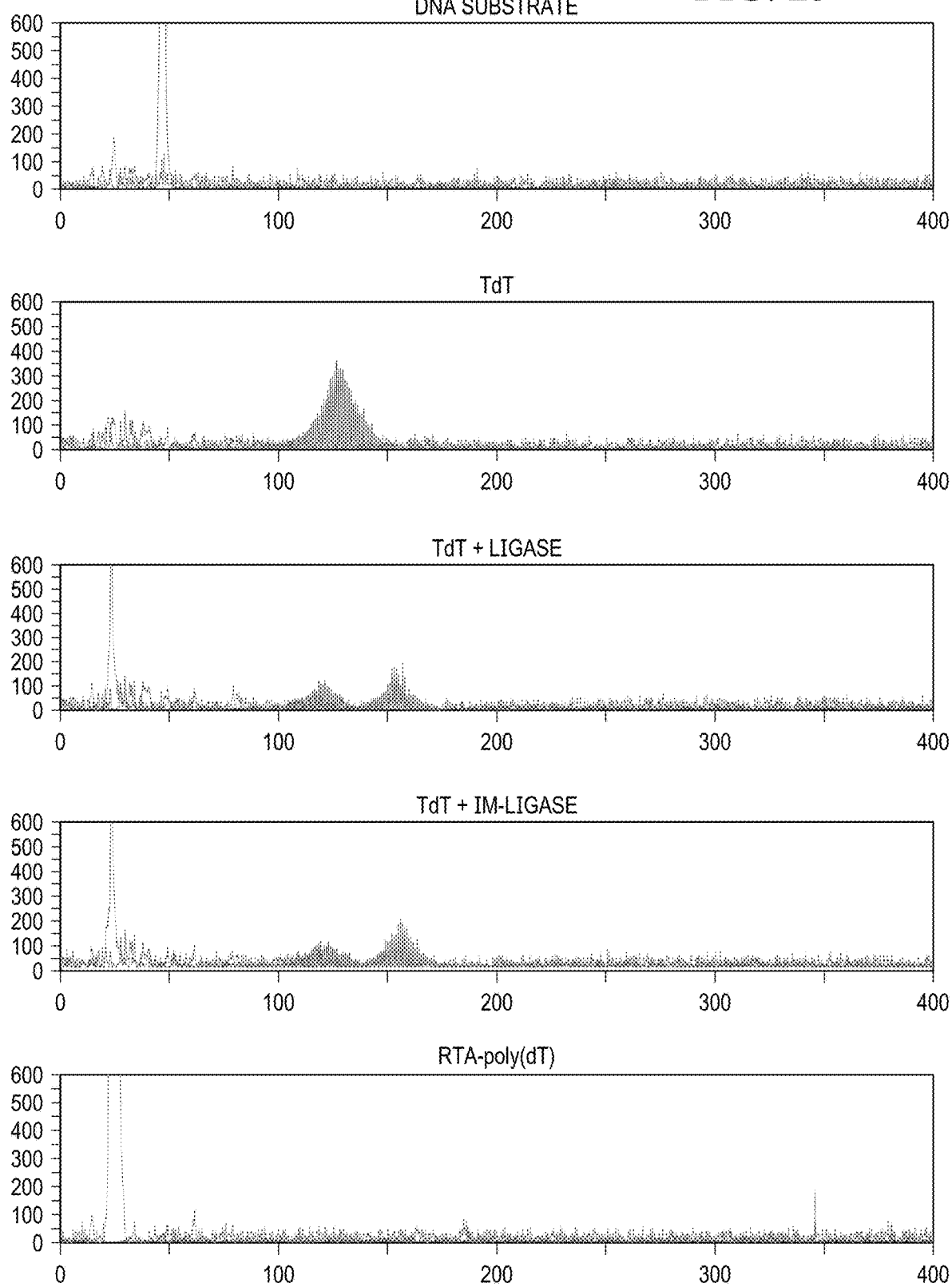

FIG. 25 shows CE analysis of sequential Poly(dA) tailing and adaptor ligation reaction products catalyzed by soluble and immobilized T4 DNA ligase. FAM-labeled DNA substrate ligated to ROX-labeled RTA-Poly(dT) by TdT in a substrate-to-dATP ratio of 1:100. Subsequently, the reaction medium containing the poly(dA)-tailed DNA products (pool), was incubated with either soluble or immobilized T4 DNA ligase and RTA-poly(dT) adaptor possessing 3' poly (dT) and ROX probe. DNA substrate: FAM-labeled DNA substrate without enzyme treatment; TdT: FAM-labeled DNA substrate treated with TdT showing multiple species corresponding to various length of poly(dA) tails; TdT+ Ligase: Poly(dA) tailed DNA treated by T4 DNA Ligase was examined with both FAM- and ROX-detecting channels (depicted in blue and red, respectively). TdT+IM-Ligase: TdT-treated DNA was treated with immobilized T4 DNA Ligase and examined with both FAM- and ROX-detecting channels (depicted in blue and red, respectively). RTA-Poly (dT): adaptor without enzymatic treatment. Co-localization of the fluorescence signals of FAM (blue) and ROX (red) indicates ligation of the 5' FAM-labeled DNA pool to the 3' ROX-labeled strand of the adaptor.

Figure 26:
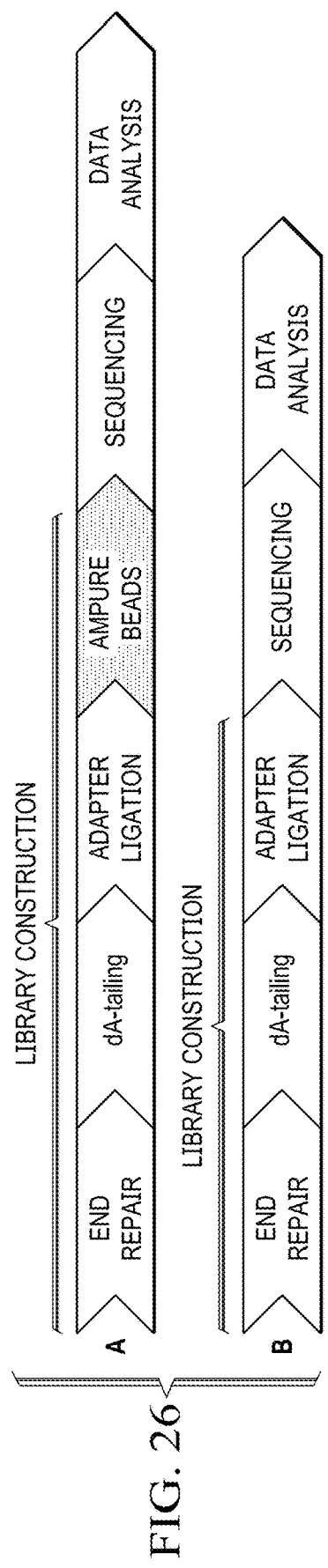

FIG. 26 shows schematic diagrams of two methods of DNA library construction. FIG. 26A shows library construction using soluble enzymes with an AMPure® bead purification step. FIG. 26B shows library construction using immobilized DNA modifying enzymes without AMPure® bead purification.

Figure 27:
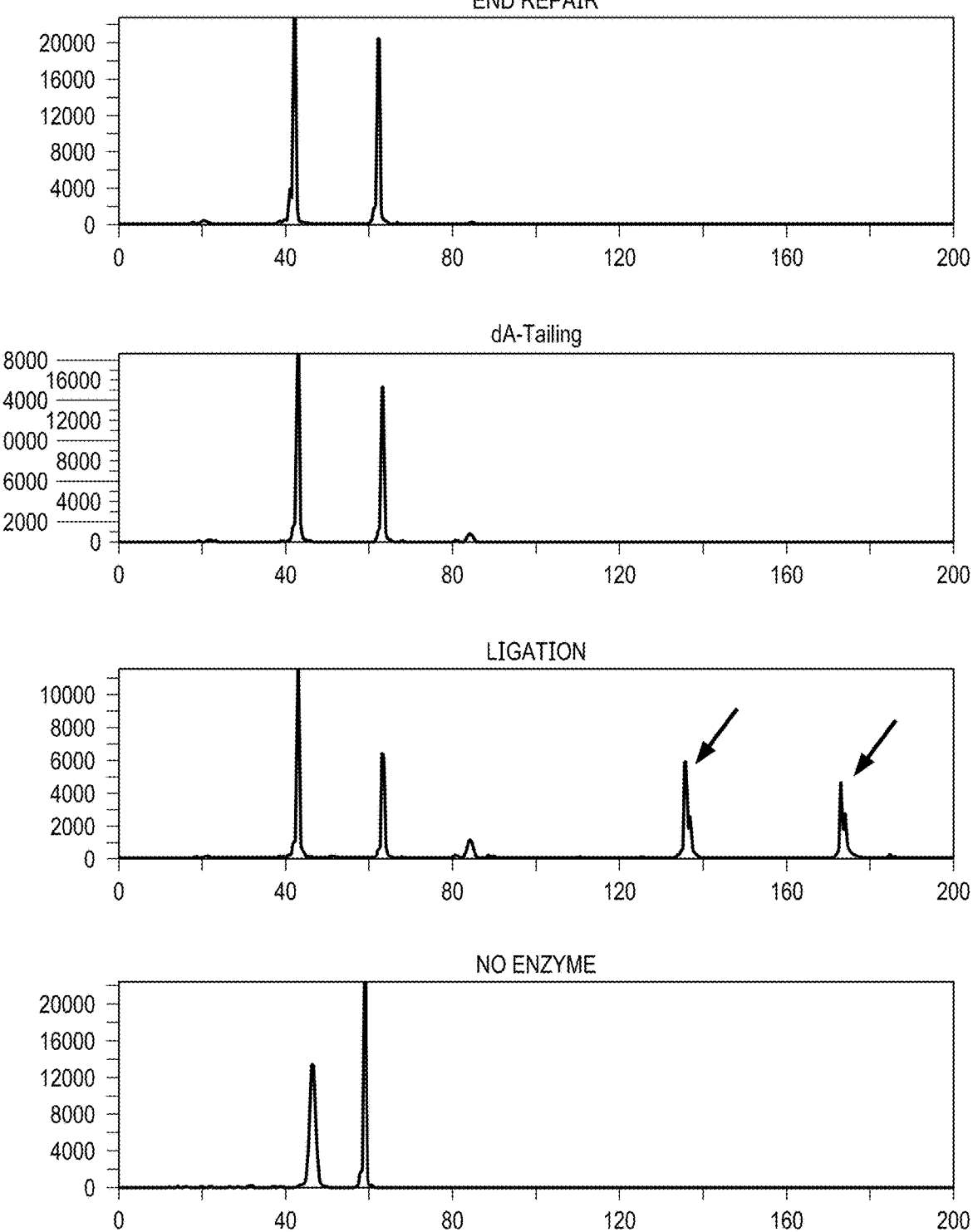

FIG. 27 shows end repair, dA-tailing and adaptor ligation of synthetic DNA modified using immobilized enzymes with products of each step subjected to CE analysis. This method is designed for construction of Nanopore DNA library without use of AMPure® bead purification and PEG-based buffer.

DETAILED DESCRIPTION

The present disclosure generally relates to methods and compositions for preparing polynucleotide libraries. Polynucleotide libraries, in some embodiments, may be prepared for sequencing using the disclosed methods and compositions. In some embodiments, compositions comprising polynucleotides (e.g., fragments) may be subjected to coupled reactions in which soluble enzymes, immobilized enzymes, or both soluble and immobilized enzymes repair or condition the ends of the polynucleotides, tail one or both ends, and/or ligate the polynucleotides to a sequencing adapter. One or more of the enzymes used may be immobilized on a bead (e.g., a magnetic bead) or other solid support. For example, in a coupled reaction comprising a tailing reaction and a ligation reaction, a tailing enzyme and a ligase may be immobilized on separate supports or co-immobilized on a common support Immobilized enzymes may reduce or obviate the need for damaging bead purification steps. Bead purification may be used to remove soluble enzymes and other compounds in the reaction media, but may also damage the polynucleotides being purified and may introduce contaminating chemicals present on the beads or in required wash solutions (e.g., ethanol and PEG among others) that may interfere with subsequent uses of the purified polynucleotides (e.g., sequencing). Library preparation methods using immobilized enzymes may require lower amounts of input polynucleotides to achieve the same number of sequencing reads and may better preserve the activity of transmembrane pores used in sequencing. Library preparation and sequencing workflows using immobilized enzymes may be automated and may include reuse of immobilized enzymes, preserving reagents and lowering costs.

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a" and "an" include plural referents unless the context clearly dictates otherwise. For example, the term "a protein" refers to one or more proteins, i.e., a single protein and multiple proteins. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified.

In the context of the present disclosure, "adapter" refers to a sequence that is joined to or can be joined to another molecule (e.g., ligated or copied onto via primer extension). An adapter can be DNA or RNA, or a mixture of the two. An adapter may be 15 to 100 bases, e.g., 50 to 70 bases, although adapters outside of this range are envisioned. In a library of polynucleotide molecules that contain an adapter (e.g., a 3' or 5' adapter, the adapter sequence used is not present in the DNA sequences under examination (i.e., the sequence in between the adapters). For example, if the library of polynucleotide molecules contains sequences derived from mammalian genomic DNA, cDNA or RNA, then the sequences of the adapters are not present in the mammalian genome under study. In many cases, the 5' and 3' adapters are of a different sequence and are not complementary. In many cases, an adapter will not contain a contiguous sequence of at least 8, 10 or 12 nucleotides that is found in the DNA under examination. Adapters may be designed to serve a specific purpose. For example, adapters may be designed for use in sequencing applications. Sequencing adapters may comprise, for example, an oligo-(dT) overhang, a barcode sequence, an overhang (other than oligo-(dT)) to anneal to another adapter, a site for anchoring a motor protein, and a sequence to bind to tethering oligos with affinity to polymer membrane for guiding a DNA or RNA fragment (on which it resides) to the vicinity of a nanopore, and combinations thereof.

In the context of the present disclosure, "adapter-containing" refers to either a nucleic acid that has been ligated to an adapter, or to a nucleic acid to which an adapter has been added by primer extension. In some embodiments, the adapters of a library of nucleic acid molecules may be made by ligating oligonucleotides to the 5' and 3' ends of the molecules (or specific sequences of the same) in an initial nucleic acid sample, e.g., DNA or genomic DNA, cDNA.

In the context of the present disclosure, "bead purification" refers to use of magnetic beads to preferentially adsorb polynucleotide molecules (e.g., RNA, DNA) away from soluble enzymes (and optionally, other components) through a series of binding, washing, and elution steps.

In the context of the present disclosure, "coupled reaction" refers to a reaction in which two or more reaction steps occur in a single reaction mixture and in a single reaction vessel (e.g., a tube, a well, a capillary, a flow cell, a surface). Sequential reaction steps in a coupled reaction may begin and/or continue without changes to reaction conditions (e.g., without addition or removal of reagents, changes in temperature, pH, volume, or washing) beyond those that arise or follow from the reactions themselves. For example, a coupled reaction may include a reaction in which a polymerase (e.g., an immobilized polymerase) is combined in a single reaction vessel with a ligase (e.g., an immobilized ligase) and both tailing and ligation reactions proceed in the same mixture (e.g., without an intervening bead purification). For clarity, coupled reactions include reactions in which microenvironments may exist (e.g., on the surface of individual microbeads in the reaction mixture).

In the context of the present disclosure, "fragment" refers to a polynucleotide. A fragment may originate from in vitro or in vivo synthetic processes. A population of fragments may include full-length polynucleotides (as originally synthesized) and/or smaller portions of such full-length sequences resulting from mechanical, chemical, and/or enzymatic breakage.

In the context of the present disclosure, "immobilized" refers to covalent attachment of an enzyme to a solid support with or without a linker. Examples of solid supports include beads (e.g., magnetic, agarose, polystyrene, polyacrylamide, chitin). Beads may include one or more surface modifications (e.g., $O^6$-benzyleguanine, polyethylene glycol) that facilitate covalent attachment and/or activity of an enzyme of interest. Non-covalent attachment (e.g., avidin:biotin, chitin:CBP) may also be useful in some embodiments, for example, where the level of dissociation of the binding partner is deemed toleratble.

In the context of the present disclosure, "library" or "polynucleotide library" refers to a mixture of different molecules. A library may comprise DNA and/or RNA (e.g., genomic DNA, organelle DNA, cDNA, mRNA, microRNA, long non-coding RNAs or other RNAs of interest) or fragments thereof from any desired source (e.g., human, non-human mammal, plant, microbe, virus, or synthetic). A library may have any desired number of different polynucleotides. For example, a library may have more than $10^4$, $10^5$, $10^6$ or $10^7$ different nucleic acid molecules. A library may have fewer different molecules, for example, where the molecules collectively have more than $10^4$, $10^5$, $10^6$ or $10^7$ or more nucleotides. In some embodiments, a library of polynucleotide molecules may be an enriched library, in which case the library may have a complexity of less than 10%, less than 5%, less than 1%, less than 0.5%, or less than 0.1%, less than 0.01%, less than 0.001% or less than 0.0001% relative to the unenriched sample (e.g., a sample made from total RNA or total genomic DNA from a eukaryotic cell sample. Molecules can be enriched by methods such as described in US2014/0287468 or US 2015/0119261. A library, in some embodiments, may include member polynucleotides that are tagged with an adapter.

In the context of the present disclosure, "ligase" refers to enzymes that join polynucleotide ends together. Ligases include ATP-dependent double-strand polynucleotide ligases, NAD+-dependent double-strand DNA or RNA ligases and single-strand polynucleotide ligases. Ligases may include any of the ligases described in EC 6.5.1.1 (ATP-dependent ligases), EC 6.5.1.2 (NAD+-dependent ligases), EC 6.5.1.3 (RNA ligases) (see ExPASy Bioinformatics Resource Portal having a URL of enzyme.expasy.org which is a repository of information concerning nomenclature of enzymes based on the recommendations of the Nomenclature Committee of the International Union of Biochemistry and Molecular Biology (IUBMB) describing each type of characterized enzyme for which an EC (Enzyme Commission) number has been provided. Specific examples of ligases include bacterial ligases such as *E. coli* DNA ligase and Taq DNA ligase, Ampligase® thermostable DNA ligase (Epicentre® Technologies Corp., part of Illumina®, Madison, Wis.) and phage ligases such as T3 DNA ligase, T4 DNA ligase, T7 DNA ligase, 9° N DNA ligase, and mutants thereof. In some embodiments, a ligase may be included in a fusion protein with a SNAP-tag protein.

In the context of the present disclosure, "magnetically gathering" refers to application of a magnetic field to a subject surface or container. A magnetic field may be applied by forming a magnetic field at or near a surface or container, or by bringing a surface or container into the effective range of an existing magnetic field, for example, by moving the surface or container near the existing field and/or by reshaping a field. Magnetically gathering immobilized enzymes into a group may include forming a pellet of immobilized enzyme. Such pellet may be sufficiently well formed and stable to tolerate manipulation or removal of a fluid, composition, or reaction mixture adjoining and/or in contact with the pellet.

In the context of the present disclosure, "non-naturally occurring" refers to a polynucleotide, polypeptide, carbohydrate, lipid, or composition that does not exist in nature. Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative).

In the context of the present disclosure, "tailing enzyme" refers to template-independent enzymes (e.g., polymerases, transferases) that add one or more nucleotides or ribonucleotides to the 3' end of a polynucleotide. Tailing enzymes may add one or more As, one or more Gs, one or more Ts, one or more Cs, or one or more Us. Tailing enzymes may be selected for specific applications based on their preference for adding a particular nucleotide or ribonucleotide, for example, to compliment the end of an adapter to which the tailed polynucleotide. Examples of tailing enzymes include poly(A) polymerases, poly(G) polymerases, poly(U) polymerases, and terminal deoxynucleotidyl transferase (TdT). In some embodiments, a tailing enzyme may be included in a fusion protein with a SNAP-tag protein.

In the context of the present disclosure, "transmembrane pore" refers to protein pores and solid state pores. A transmembrane pore may be a nanopore. Transmembrane protein pores may be or comprise hemolysin, leucocidin, lysenin, a *Mycobacterium smegmatis* porin (e.g., MspA, MspB, MspC, MspD), CsgG, an outer membrane porin (e.g., OmpF, OmpG), outer membrane phospholipase A, *Neisseria* autotransporter lipoprotein (NalP), WZA, or variants thereof.

In the context of the present disclosure, "unique molecule identifier" (UMI) refers to a random unique sequence of at least 6 nucleotides (6N). Longer random unique sequences may be used, for example, 2-15 nucleotides, 6-12 nucleotides, or 8-12 nucleotides. UMIs may have sufficient sequence diversity to distinguish the molecule of which they are a part (e.g., an adapter or a tagged fragment) from other molecules in a mixture.

All publications (including all co-published supplemental and supporting information), patents, and patent applications mentioned in this specification are herein incorporated by reference to the same extent as if each individual publication, patent, or patent application was specifically and individually indicated to be incorporated by reference.

Figure 1C:
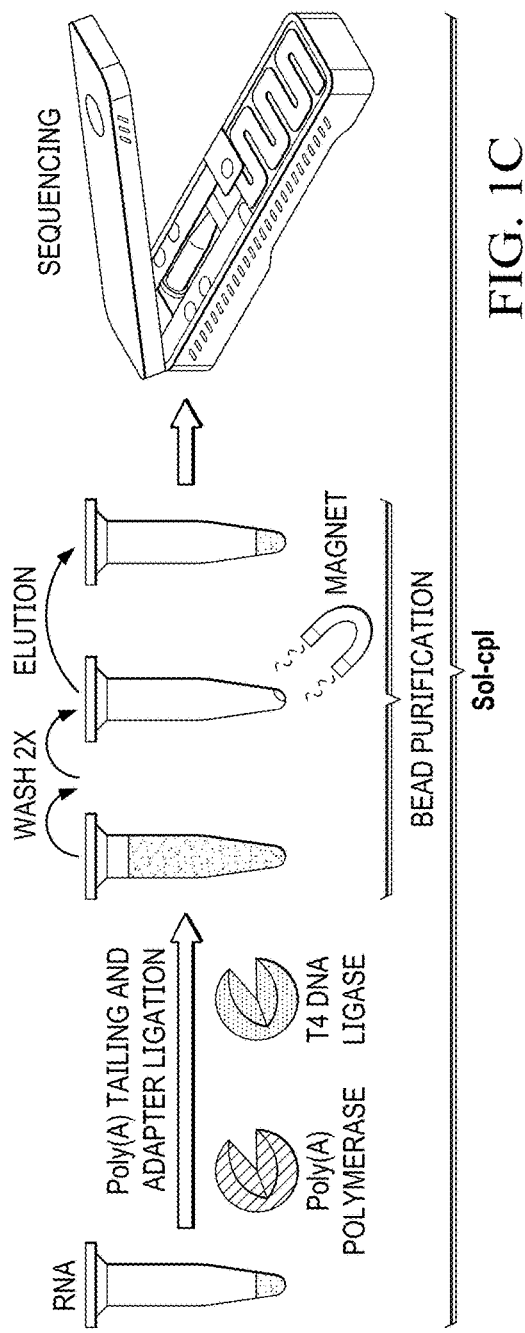

FIG. 1A-E illustrates some embodiments of methods and compositions disclosed herein. For example, a method may include sequentially contacting an RNA composition (e.g., comprising one or more species of RNA molecules) and a soluble tailing enzyme (optionally in the presence of a buffer) to produce a polyA tailed RNA composition, contacting the polyA tailed RNA composition with an adapter and a soluble ligase to produce ligated products, washing the ligated products, eluting the ligated products, and sequencing the ligated products (FIG. 1A).

A coupled method may include contacting an RNA composition (e.g., comprising one or more species of RNA molecules), a soluble tailing enzyme, an adapter, and a soluble ligase (optionally in the presence of a buffer) to produce ligated products, washing the ligated products, eluting the ligated products, and sequencing the ligated products (FIG. 1B).

A method, in some embodiments, may include sequentially contacting an RNA composition (e.g., comprising one or more species of RNA molecules) and a soluble tailing enzyme (optionally in the presence of a buffer) to produce a polyA tailed RNA composition, contacting the polyA tailed RNA composition with an adapter and a soluble ligase to produce ligated products, and directly (e.g., without washing or elution) sequencing the ligated products (FIG. 1C).

Figure 1D:
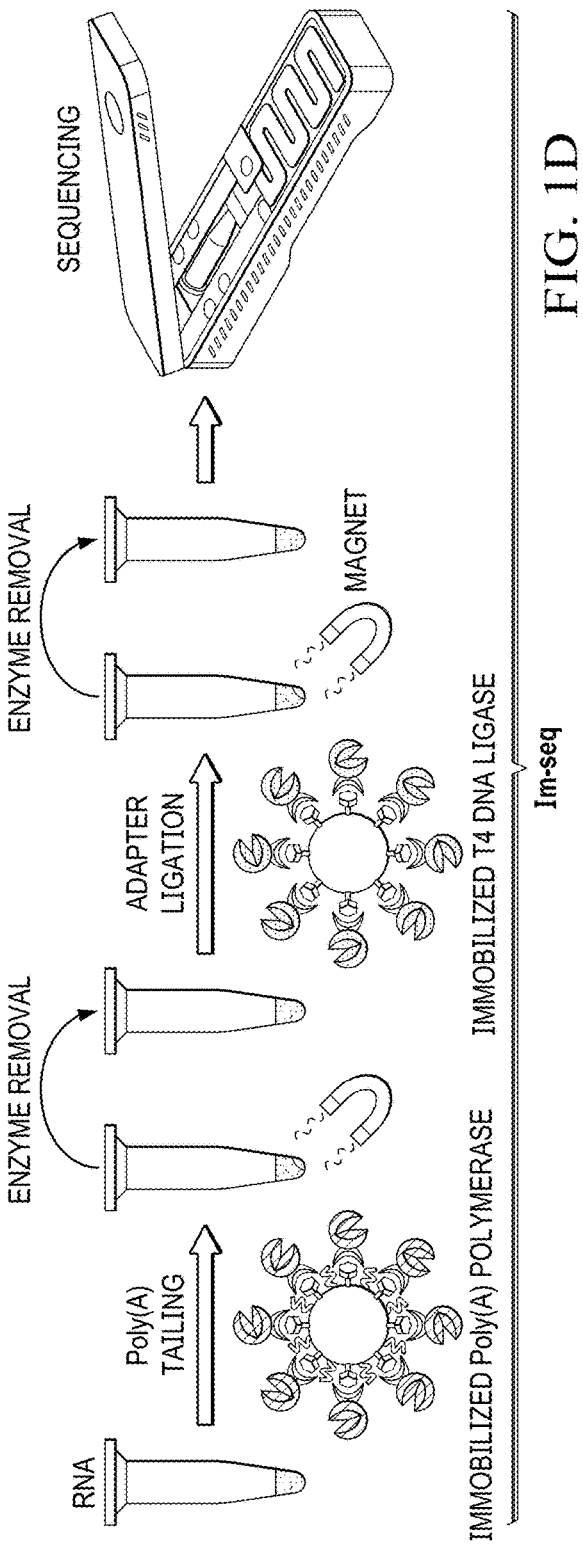

In some embodiments, a method may include sequentially contacting an RNA composition (e.g., comprising one or more species of RNA molecules) and an immobilized tailing enzyme (optionally in the presence of a buffer) to produce a polyA tailed RNA composition, removing the immobilized tailing enzyme (e.g., in the case of enzymes bound to magnetic beads, magnetically gathering the magnetic beads into a group and taking away the polyA tailed composition, for example, by pipetting away from the beads), contacting the polyA tailed RNA composition with an adapter and an immobilized ligase to produce ligated products, removing the immobilized ligase (e.g., in the case of enzymes bound to magnetic beads, magnetically gathering the magnetic beads into a group and taking away the ligated products, for example, by pipetting away from the beads), and directly (e.g., without further washing or elution) sequencing the ligated products (FIG. 1D).

Figure 1E:
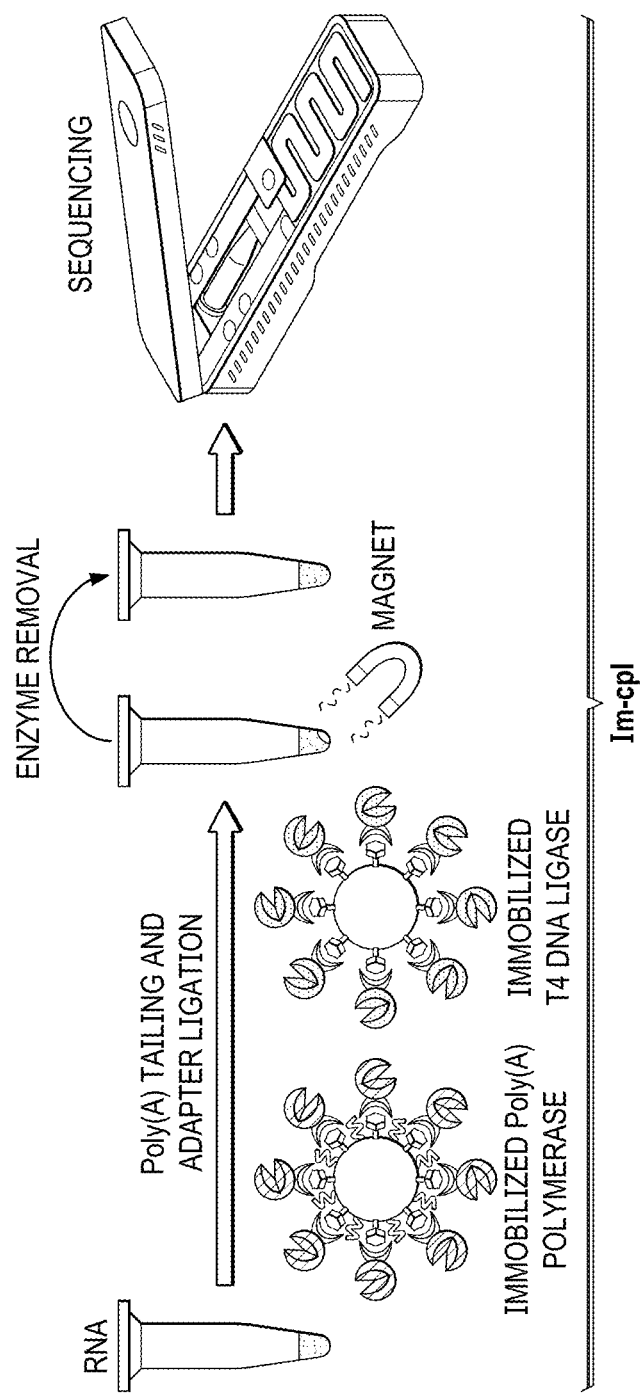

A coupled method, in some embodiments, may include contacting an RNA composition (e.g., comprising one or more species of RNA molecules), an immobilized tailing enzyme, an adapter, and an immobilized ligase (optionally in the presence of a buffer) to produce ligated products, removing the immobilized tailing enzyme and the immobilized ligase (e.g., in the case of enzymes bound to magnetic beads, magnetically gathering the magnetic beads into a group and taking away the ligated products, for example, by pipetting away from the beads), and directly (e.g., without further washing or elution) sequencing the ligated products (FIG. 1E).

With respect to its corresponding soluble enzyme, an immobilized enzyme is physically constrained to a support which defines a microenvironment for the immobilized enzyme molecules and its substrates. Surface environments (e.g. charges, functional groups, morphology, hydrophilicity) of the support materials can effect the enzymatic rate and immobilized enzyme stability. Therefore, improving and optimizing this microenvironment may enhance or maximize enzymatic activities upon immobilization. One or more strategies to alter surface microenvironment may be used to improve activity of immobilized enzymes. A single optimization solution may not applicable to all the enzymes. In some embodiments, various blocking groups or bead coatings (ethanolamine and polyethylene glycol—PEG of different lengths) can be utilized to modify hydrophilicity of support surface. For example, polyethylene glycol (PEG) moieties can be used to modify the surface of BG-functionalized magnetic beads. This PEG coating strategy has been shown to be effective in enhancing activity of several enzymes validated, including T4 DNA polymerase, Taq DNA polymerase and T4 DNA ligase) (Li et al. 2018). According to some embodiments, the distance between the immobilized enzyme and the beads surface may play a key role in retaining or reducing enzymatic activity. By using the proper conjugation chemistry, polyethylene glycol (PEG) linkage groups with variable length can be applied as a spacer in between a SNAP-reactive BG and the bead surface. Various benzylguanine (BG) moieties (with PEGlated or non-PEGylated linkers) may confer different spatial arrangement of conjugated enzyme molecules. In some embodiments, solid phase catalysis strategically considers the substrate properties and accessibility which can be affected by surface properties and enzyme orientation. In addition, CLIP-reactive benzylcytosine (BC) moieties can be utilized to substitute for BG moieties on solid support because BC moieties are considered to be more hydrophilic than BG moieties. With this strategy, a target enzyme is fused to CLIP-tag instead of SNAP-tag. According to some embodiments, a bio-orthogonal conjugation strategy can simultaneously co-immobilize two enzymes in a desired molar ratio onto beads functionalized with SANP-reactive BG and CLIP-reactive BC moieties. Selection of support materials and proper modifications may enhance enzymatic activity and thermostability. The surface properties can modulate refolding upon relaxation and denaturation of enzyme globular structures thereby maintaining or regaining activity after storage and heat treatment.

Figure 14:
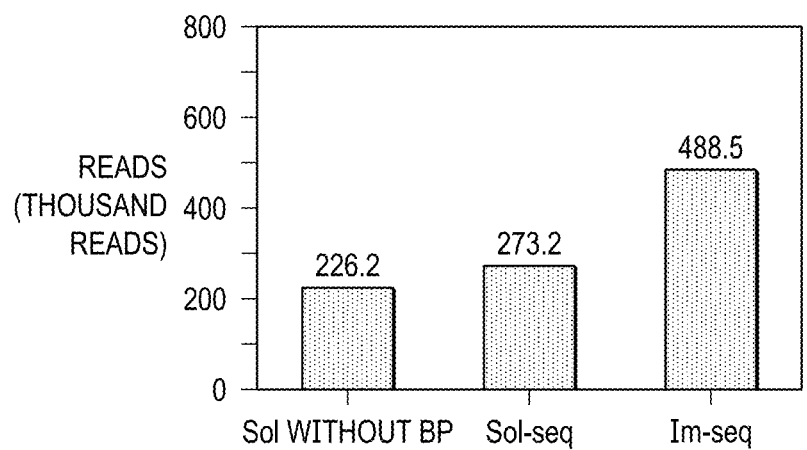
FIG. 14 compares Nanopore RNA sequence reads obtained with libraries prepared by different methods. Each library was prepared using soluble enzymes without bead purification (Sol w/o BP), soluble enzymes with sequential poly(A) tailing and ligation with bead purification (Sol-seq), or immobilized enzymes with sequential poly(A) tailing and ligation protocol without bead purification (Im-seq). 164 ng of RNA library was used for each sequencing run.
Figure 19:
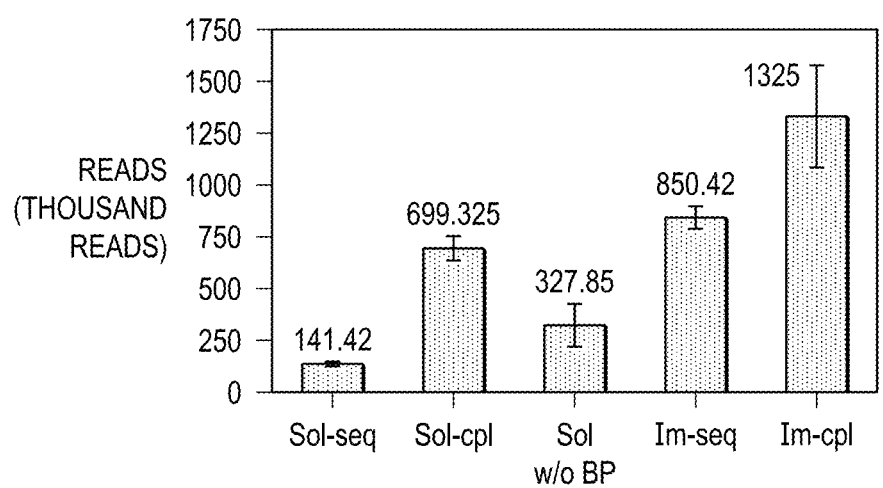
FIG. 19 shows a comparison of the number of Nanopore RNA sequencing reads obtained with RNA libraries prepared according to one of five methods: Sol-seq libraries were prepared with soluble enzymes and bead purification using a sequential reaction protocol; Sol-cpl libraries were prepared with soluble enzymes and bead purification using a coupled reaction protocol; Sol w/o BP libraries prepared with soluble enzymes sequentially without bead purification; Im-seq libraries were prepared with immobilized enzymes using the sequential reaction protocol without bead purification; Im-cpl libraries were prepared with immobilized enzymes using the coupled reaction protocol without bead purification. The sequencing reads shown were obtained after 2 hour run time.

In RNA sequencing reactions or other applications using nanopores, the nanopores may be clogged, inactivated, and/or otherwise compromised by proteins that may be present in the compositions contacted with the nanopores. Accordingly, methods, applications, protocols and workflows including nanopores may comprise removing proteins (e.g., soluble proteins) by bead purification to alleviate such fouling. In some embodiments, the need for bead purification may be reduced or obviated by optimizing enzymatic reactions, for example, by reducing the amounts of enzymes used (e.g., effectively decreasing the ratio of enzyme to product in a reaction). Reducing the amount of enzyme(s) may reduce nanopore fouling thereby extending the functional time of nanopores in flow cells. While a reduction in the quantity of enzymes used may apply to all proteins or all enzymes in a reaction, since each protein and enzyme may interact with a given nanopore differently, reductions may be made on a more selective basis, targeting those that are more prone to fouling. As explained in more detail in the Example section below, FIG. 14 & FIG. 19 show that it is possible to generate sequence reads from libraries without bead purification, confirming that optimization of reactions with soluble enzymes enhance library preparation and/or performance.

In some embodiments, a wide range of enzymes may be immobilized without loss or without substantial loss of activity including, for example, Taq DNA polymerase, T4 DNA polymerase (T4 DNA pol), T4 polynucleotide kinase (T4 PNK), T4 DNA ligase, polyA polymerase, Klenow (Exo-), T4 BGT, 9° N DNA ligase, Taq DNA ligase, Bst DNA pol 2.0, phi29 DNA pol, Vvn (nuclease), Gka Reverse transcriptase, Tbr Reverse transcriptase, RNase A (catalytic mutants), PolyA polymerase, Beta-galactosidase, PNGaseF, Endo H, Endo S, Sialidase, Human carbonyl reductase, Human Aldose reductase, *Drosophila* aldehyde-ketone reductase (AKR).

For example, the current ONT protocol uses 3 ul of T4 DNA Ligase (NEB M202M 2000 units/ul) or 6000 units for 500 ng input library. Use of immobilized enzymes and/or coupled reactions may reduce the amount of soluble T4 DNA Ligase by 90% (i.e. use of 600 units of ligase) because the immobilized enzyme protocols validated used only 180 units. For low input RNA library (<100 ng input), enzyme consumption can be further lowered.

Enzyme immobilization may provide opportunities to enhance performance of enzymatic processes, for example, by allowing faster and more efficient production of products, at least in part, by reducing or eliminating purification steps needed for corresponding soluble enzyme processes, by reducing reactant and/or product losses from washing steps, and/or by allowing enzymes to be reused in subsequent reaction cycles Immobilization may imbue bound enzymes with additional thermostability and/or thermoactivity. For example, immobilized enzymes may tolerate higher temperatures (even if they are not catalytically active at such higher temperatures), which could be useful for applications in which enzymes are reused. In some embodiments, enzyme immobilization may allow soluble enzyme processes to be automated (or automated more efficiently) Immobilization may also allow processes to be more effective and/or efficient by reducing enzyme carry over to subsequent steps.

In some embodiments, methods including immobilized enzymes may omit or exclude heat treatments to inactivate enzymes, bead purification steps, and/or sequencing pore clogging. Heat stress can lead to the accumulation of 8-oxoguanine, deaminated cytosine, and apurinic DNA sites (AP-sites) in a cell (Bruskov V. I., Malakhova L. V., Masalimov Z. K., Chernikov A. V.//Nucleic Acids Res. 2002. V. 30. P. 1354-1363. 19. Lindahl T., Nyberg B.//Biochemistry. 1974. V. 13. P. 3405-3410. 20. Warters R. L., Brizgys L. M.//J. Cell Physiol. 1987. V. 133. P. 144-150. Elimination of bead purification may result in more uniformly sized fragments in a library to be sequenced. Bead purification may result in alteration of a library such as size distribution; For example, large or small species may be lost more than the species in the middle size range due to either less binding (leading to more loss) or tighter binding resulting in lower elution efficiencies. This step may also introduce impurities (present in loading and wash solutions) that may affect performance or parameters of nanopores such as signals or functioning time.

According to some embodiments, methods including immobilized enzymes may be adapted to and performed in microfluidic, lab-on-a-chip formats with enzymes immobilized on surfaces. For example, systems for single-cell RNA sequencing that produce RNA of a single cell may be adapted to contact such RNA with a tailing enzyme and a ligase (coupled or sequentially) on a surface or in a microfluidics device.

The present disclosure provides embodiments in which purification of nucleic acids is facilitated by combining enzymatic steps into a single reaction and/or immobilizing enzymes on magnetic beads or other supports. The present disclosure further provides embodiments in which enzyme activity and/or thermostability is enhanced by immobilization on magnetic beads or other supports.

In some embodiments, a method of preparing a library (e.g., a DNA library, an RNA library) for sequencing (e.g., ONT sequencing) may include in a coupled reaction, (a) contacting a population of nucleic acid fragments with a tailing enzyme to produce tailed fragments, and/or (b) ligating to the tailed fragments a sequencing adapter with a ligase to produce adapter-tagged fragments. A method may further include separating adapter-tagged fragments from the tailing enzyme and the ligase to produce separated adapter-tagged fragments and optionally separated tailing enzyme and/or separated ligase. A tailing enzyme, in some embodiments, may be or comprise immobilized tailing enzyme. A ligase, in some embodiments, may be or comprise immobilized ligase. For example, a tailing enzyme may be immobilized on a bead (e.g., a magnetic bead) and/or a ligase may be immobilized on a bead (e.g., a magnetic bead). Each immobilized enzyme may be attached to a separate support or may be combined on a common support. Optionally, a tailing enzyme and a ligase each may be immobilized on their own separate support or both may be co-immobilized on a single support. In some embodiments, one or more enzymes (e.g., a tailing enzyme and/or a ligase) may be soluble enzymes. For example, a method may include contacting one or more soluble enzymes with one or more substrates in a liquid (e.g., aqueous) media. In some embodiments, a method may include contacting two enzymes (e.g., a tailing enzyme and a ligase) with at least one substrate for at least one of the two enzymes (e.g., DNA or RNA) in a coupled reaction. In some embodiments of a coupled reaction, at least one product of one of the enzymes is a substrate of the other enzyme. It may be desirable to select reaction conditions to favor production of the product(s) that are substrates of the other enzyme and minimize or avoid production of anything that reduces the efficiency of any of the coupled reaction enzymes, but conditions may be adjusted to tolerate the presence of some unwanted products.

In some embodiments, separating adapter tagged fragments (e.g., where one or more enzymes used are immobilized on magnetic beads) may further comprise subjecting the coupled reaction to a magnetic field. Subjecting a coupled reaction to a magnetic field may include accomplished in any manner desired. For example, a coupled reaction may be moved into an existing magnetic field, an existing magnet may be moved into effective range of a coupled reaction, or a magnetic field may be applied, for example, by switching on an electromagnet within an effective distance of a coupled reaction. In some embodiments, subjecting a coupled reaction to a magnetic field gathers magnetic beads in the coupled reaction forming a liquid fraction comprising, for example, reaction products, buffers, and solvent, but few, if any, magnetic beads) and a bead fraction comprising, for example, magnetic beads, enzymes, and solvent, but few, if any, reaction products. Gathered magnetic beads may form a pellet or other aggregate that facilitates separation (e.g., removal) of other reaction components (e.g., components remaining in solution).

A population of nucleic acid fragments may comprise ribonucleic acid fragments and/or may comprise deoxyribonucleic acid fragments. Fragments may be of any desired size. For example, a population of nucleic acid fragments may comprise fragments ranging in length from 100 to 1000 nts, 200 to 2000 nts, 500 to 5000 nts, 1,000 to 10,000 nts, 2,000 to 20,000 nts, 5,000 to 50,000 nts, 10,000 to 100,000 nts, or combinations thereof. A population of nucleic acid fragments may comprise fragments from any desirable source including, for example, fragments synthesized or assembled in vitro and/or fragments of polynucleotides from microbes (e.g., yeast, bacteria, viruses, phage), fungi, plants, amphibians, reptiles, fish, mammals, birds, or any other organism.

In some embodiments, methods may be capable of producing sequencing libraries with little input RNA. For example, methods may use a population of nucleic acid fragments having less than 100 ng of nucleic acids or a population of nucleic acid fragments having less than 10 ng of nucleic acids. In some embodiments, methods including coupled reactions and/or immobilized enzymes may produce more sequencing reads per mass of input DNA or RNA when compared with corresponding methods that do not include coupled reactions and/or immobilized enzymes. For example, methods including a coupled reaction and/or an immobilized enzyme may produce 2×, 3×, 4×, 5×, 6×, 7×, 8×, 9×, 10×, 11×, 12× or more sequencing reads compared to methods including only sequential reactions with soluble enzymes and bead purification.

The present disclosure further provides methods for preparing sequencing libraries comprise any combination of tailing and/or ligating steps and further comprising reusing the tailing enzyme and/or the ligase. For example, a method may include, in a second reaction (e.g., a second coupled reaction), contacting a second population of nucleic acid fragments with the separated tailing enzyme (produced from the first reaction) to produce additional tailed fragments, and ligating (optionally, with a ligase also recycled from the first reaction) to the additional tailed fragments a second sequencing adapter with the separated ligase to produce additional adapter-tagged fragments. The additional adapter-tagged fragments may be separated from the separated tailing enzyme and the separated ligase to produce separated additional adapter-tagged fragments, separated tailing enzyme, and/or separated ligase.

In some embodiments, a method contacting separated adapter-tagged fragments with one or more transmembrane pores (e.g., ONT nanopores) for sequencing. For example, a method may comprise translocating separated adapter-tagged fragments through one or more transmembrane pores, (f) detecting electrical changes as the one or more separated adapter-tagged fragments are translocated through the one or more transmembrane pores in an insulating membrane to produce an electrical signal; and/or analyzing the electrical signal to generate a sequence read. In some embodiments, one or more transmembrane pores (e.g., in contact with a population of adapter-tagged fragments) may retain about 90% of their initial activity (e.g., translocation activity) after two hours and/or may retain about 50% of their initial activity after 8 hours. One or more transmembrane pores, according to some embodiments of the disclosure, may produce at least 900 sequence reads per transmembrane pore. For example, the number of sequencing reads of a population of nanopores (e.g., in contact with a population of adapter-tagged fragments) may be, on average, at least 900. In some embodiments, a sequencing adapter may be a single-stranded adapter and may comprise a leader sequence; and a first sequence and a second sequence, wherein the first and second sequences are complementary to each other and define a hairpin, wherein the leader sequence is configured to thread into the one or more transmembrane pores.

Kits

The present disclosure further relates to kits including immobilized enzymes. For example, a kit may include an immobilized tailing enzyme, an immobilized ligase, a polynucleotide (e.g., a population of polynucleotides) dNTPs, rNTPs, primers, buffering agents, and/or combinations thereof. Immobilized enzymes may be included in a storage buffer (e.g., comprising glycerol and a buffering agent). A kit may include a reaction buffer which may be in concentrated form, and the buffer may contain additives (e.g. glycerol), salt (e.g. KCl), reducing agent, EDTA or detergents, among others. A kit comprising dNTPs may include one, two, three of all four of dATP, dTTP, dGTP and dCTP. A kit comprising rNTPs may include one, two, three of all four of rATP, rUTP, rGTP and rCTP. A kit may further comprise one or more modified nucleotides. A kit may optionally comprise one or more primers (random primers, bump primers, exonuclease-resistant primers, chemically-modified primers, custom sequence primers, or combinations thereof). One or more components of a kit may be included in one container for a single step reaction, or one or more components may be contained in one container, but separated from other components for sequential use or parallel use. The contents of a kit may be formulated for use in a desired method or process.

A kit is provided that contains: (i) an immobilized tailing enzyme; and (ii) a buffer or (i) an immobilized tailing enzyme; (ii) an immobilized ligase, and (iii) a buffer. An immobilized enzyme may have a lyophilized form or may be included in a buffer (e.g., an aqueous buffer, a storage buffer or a reaction buffer in concentrated form). A kit may contain the immobilized enzyme in a mastermix suitable for receiving and amplifying a template nucleic acid. An immobilized enzyme may be a purified enzyme so as to contain substantially no DNA or RNA and/or no nucleases. A reaction buffer for and/or storage buffers containing an immobilized enzyme may include non-ionic, ionic e.g. anionic or zwitterionic surfactants and crowding agents. A kit may include an immobilized enzyme and a reaction buffer in a single tube or in different tubes.

A subject kit may further include instructions for using the components of the kit to practice a desired method. The instructions may be recorded on a suitable recording medium. For example, instructions may be printed on a substrate, such as paper or plastic, etc. As such, the instructions may be present in the kits as a package insert, in the labeling of the container of the kit or components thereof (i.e., associated with the packaging or sub-packaging) etc. Instructions may be present as an electronic storage data file residing on a suitable computer readable storage medium (e.g. a CD-ROM, a flash drive). Instructions may be provided remotely using, for example, cloud or internet resources with a link or other access instructions provided in or with a kit.

EXAMPLES

Some embodiments may be illustrated by one or more of the examples provided herein.

Example 1: Immobilization of Poly(A) Polymerase and Kinetics Study

Example 1A. Soluble Poly(A) Polymerase Alone

Poly(A) polymerase catalyzes poly(A) tailing at the 3' end of RNA and the resulting tails can be hybridized with and ligated to adapters (e.g., Nanopore Adaptors) for direct RNA sequencing. The kinetics of poly(A) polymerase (NEB M0276) at different concentrations was studied as described in this Example 1. Reaction components (6 µL nuclease-free water, 1 µL, 10× poly(A) polymerase reaction buffer (NEB), 1 µL 10 mM ATP, 0.5 µL RNase inhibitor, 1 µL 1 µM RNA 45-mer oligo and 0.5 µL poly(A) polymerase (at 12 nM, 24 nM, 60 nM or 120 nM)) were mixed and incubated at 37° C. for 20 mM to allow poly(A) tailing. Each reaction was quenched by addition of 10 µL 50 mM EDTA with 0.7% Tween-20, diluted to a final volume of 200 µL, and sent for capillary electrophoresis (CE) analysis.

Figure 2:
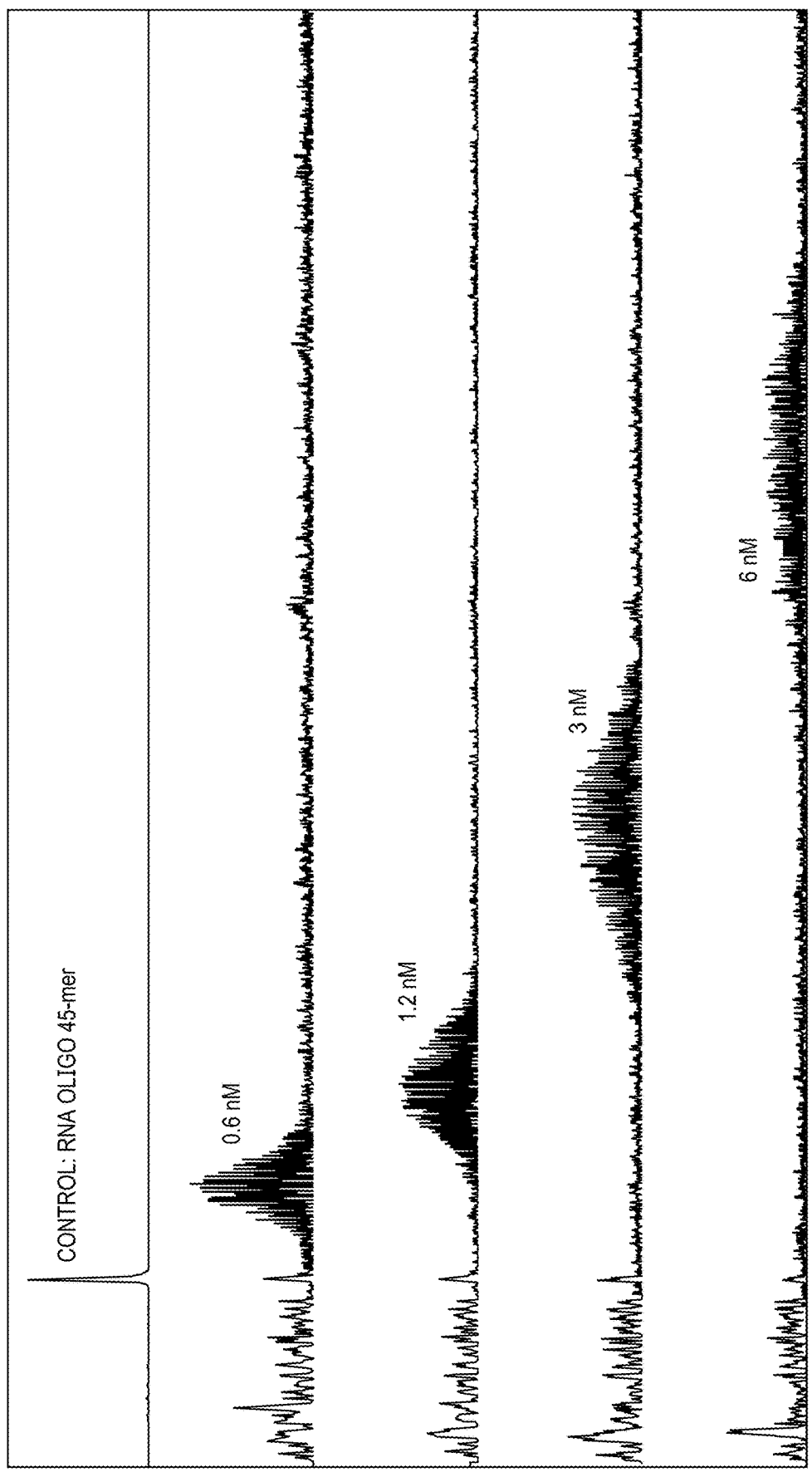
FIG. 2 shows that poly(A) extension is dependent on poly(A) polymerase concentration. An RNA 45-mer oligo strand was treated with different concentrations of untagged poly(A) polymerase from NEB and poly(A) tailing activity of poly(A) polymerase was evaluated by capillary electrophoresis (CE).

Results shown in FIG. 2 demonstrate that RNA oligo strands were extended by addition of poly(A) tails at the 3' end of the RNA with the presence of poly(A) polymerase. More extensive strand extension was observed with increasing the concentration of poly(A) polymerase from 0.6 nM to 6 nM final concentration.

Example 1B. Poly(A) Polymerase—SNAP-Tag® Fusion

Cells expressing a poly(A) polymerase—SNAP-Tag® fusion were harvested by centrifugation and lysed by sonication on ice. The resulting lysate was centrifuged and the clarified crude extract produced was purified on a nickel column. After loading, the column was washed and the fusion protein was eluted and dialyzed overnight. The enzyme concentration was determined using Bradford assay.

Figure 3:
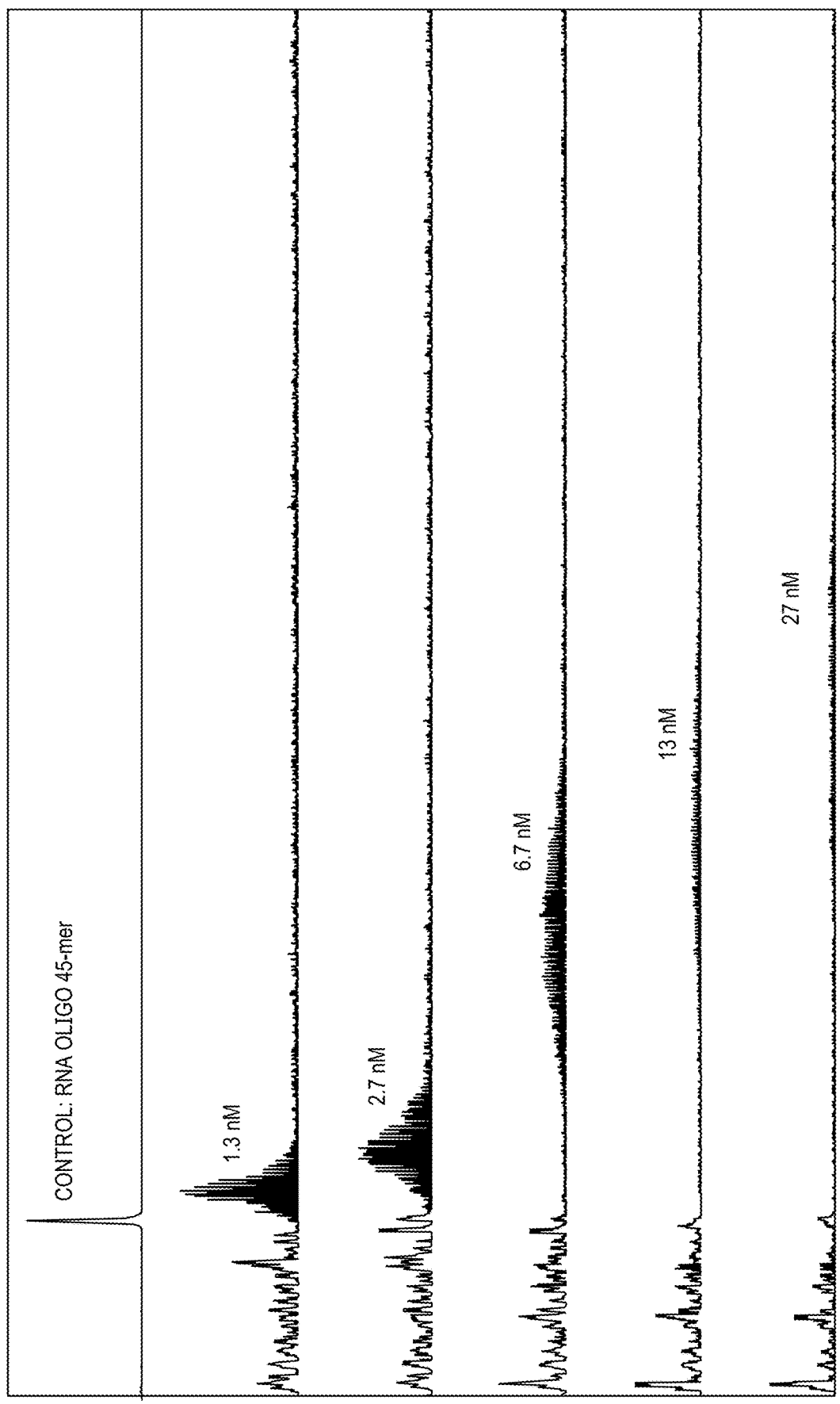
FIG. 3 shows that poly(A) extension is dependent on the concentration of poly(A) polymerase—SNAP fusion protein. An RNA 45-mer oligo strand was treated with different concentrations of a poly(A) polymerase—SNAP fusion protein and poly(A) tailing activity of was evaluated by capillary electrophoresis (CE).

The activity of the expressed fusion protein was evaluated according to Example 1A. Results shown in FIG. 3 demonstrate RNA 45-mer oligo strand extension by the purified poly(A) polymerase—SNAP fusion protein. Comparing FIG. 2 and FIG. 3 demonstrates that RNA 45-mer oligo strand extension by the poly(A) polymerase—SNAP fusion protein aligned well with the soluble NEB poly(A) polymerase.

Figure 4:
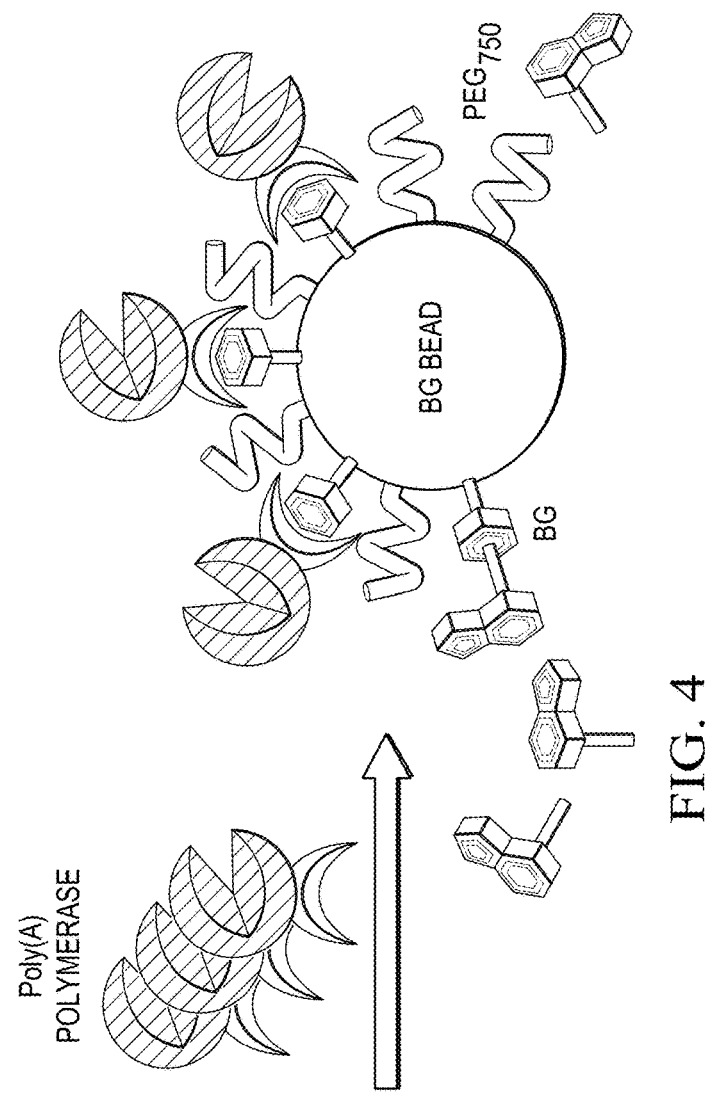
FIG. 4 shows poly(A) polymerase immobilization on $PEG_{750}$ coated $0^6$-benzylguainine (B G) beads.
Figure 4:
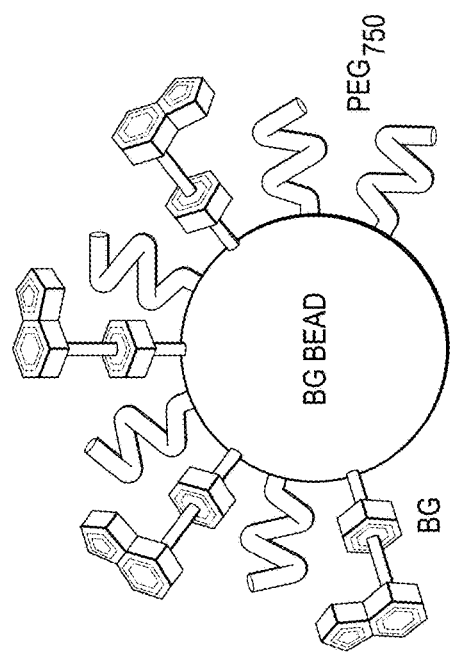

Example 1C. Poly(A) Polymerase Immobilization on $O^6$-Benzylguainine (BG) Magnetic Beads $O^6$-benzylguainine (BG) functionalized magnetic beads coated with $PEG_{750}$ (100 µL of a 25% (v/v) slurry) were washed five times with 250 µL buffer (1×PBS, #9808, Cell Signaling, 1 mM DTT, 300 mM NaCl) for 5 times. Poly(A) polymerase—SNAP fusion protein (25 µg) in 125 µL buffer (1×PBS with 300 mM NaCl), was mixed with the pre-washed BG beads, and incubated at 4° C. overnight to immobilize the fusion protein (FIG. 4). The enzyme bead mixture was washed with the same buffer 8 times to remove unbound protein. Diluent C buffer without BSA (NEB) was used to resuspend the beads with immobilized fusion protein for storage at −20° C.

Figure 5:
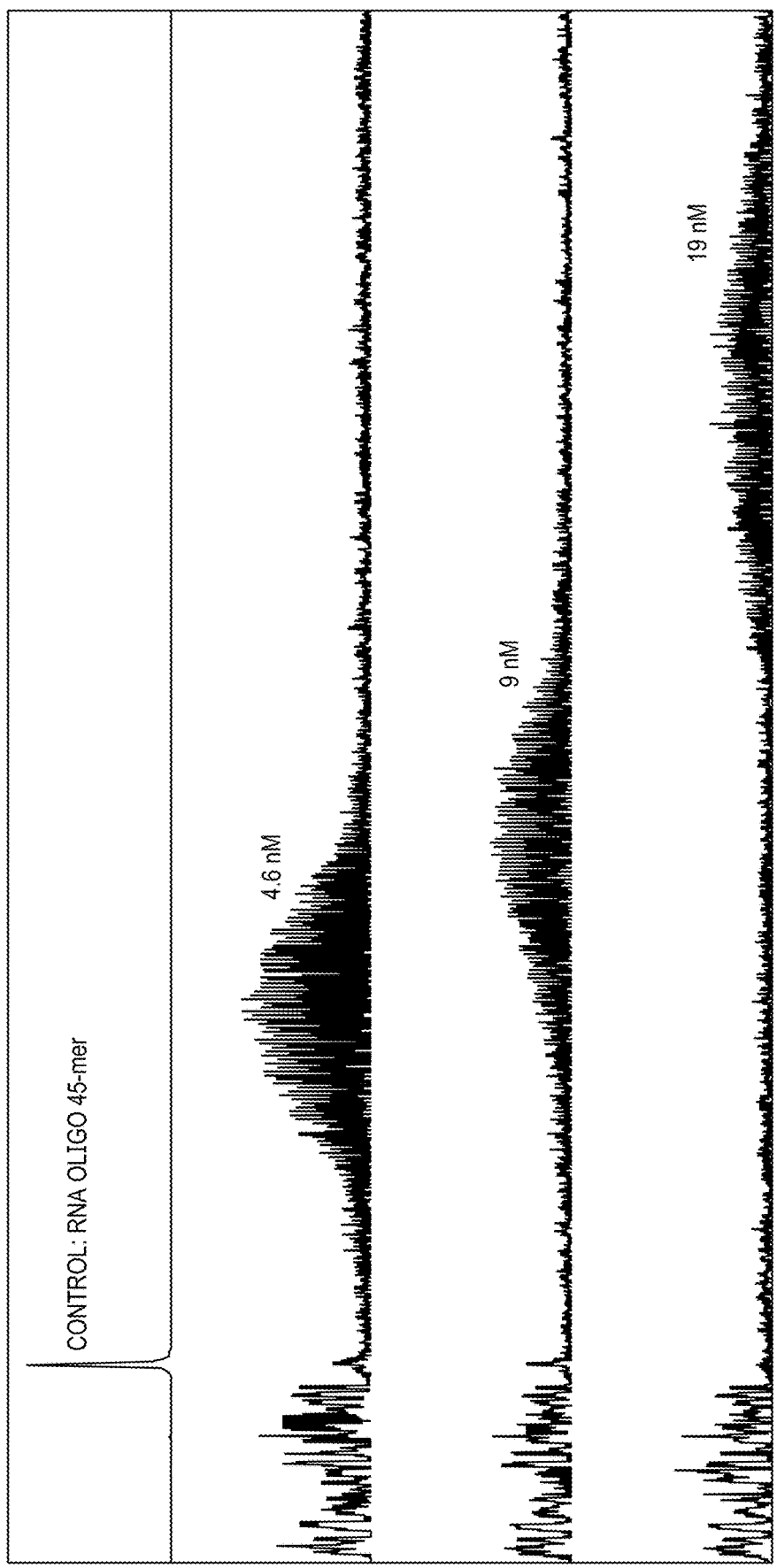
FIG. 5 shows that poly(A) extension is dependent on the concentration of an immobilized poly(A) polymerase. An RNA 45-mer oligo strand was treated with different concentrations of an immobilized poly(A) polymerase and poly(A) tailing activity was evaluated by capillary electrophoresis (CE).

The activity of the immobilized poly(A) polymerase was evaluated according to Example 1A. Results shown in FIG. 5 demonstrate RNA 45-mer oligo strand extension by the immobilized poly(A) polymerase—SNAP fusion protein.

Example 2: Immobilized Poly(a) Polymerase Displays Stability Including Thermostability This example shows how to improve microenvironment for immobilized enzymes by increasing hydrophilicity of bead surface by PEG coating. Poly(A) polymerase was immobilized to two types of $O^6$-benzylguainine (BG) functionalized magnetic beads coated with or without $PEG_{750}$ generally as described in Li, S et al, "Enhancing Multistep DNA Processing by Solid-Phase Enzyme Catalysis on Polyethylene Glycol Coated Beads" *Bioconjugate Chem.* 2018, 29, 7, 2316-2324 An aliquot of 100 µL of 25% (v/v) bead slurry was washed five times with 250 µL buffer (1×PBS, #9808, Cell Signaling, 1 mM DTT, 300 mM NaCl) for 5 times. Poly(A) polymerase—SNAP fusion protein (25 µg) was dissolved in 125 µL buffer (1×PBS with 300 mM NaCl), combined with the washed BG beads, and incubated at 4° C. overnight to immobilize the fusion protein on the beads. The immobilized poly(A) polymerase—SNAP fusion protein beads were washed with the same buffer 8 times to remove any unbound protein. Diluent C buffer (NEB) with no BSA was used to resuspend the beads with immobilized fusion protein for storage at −80° C.

Figure 6:
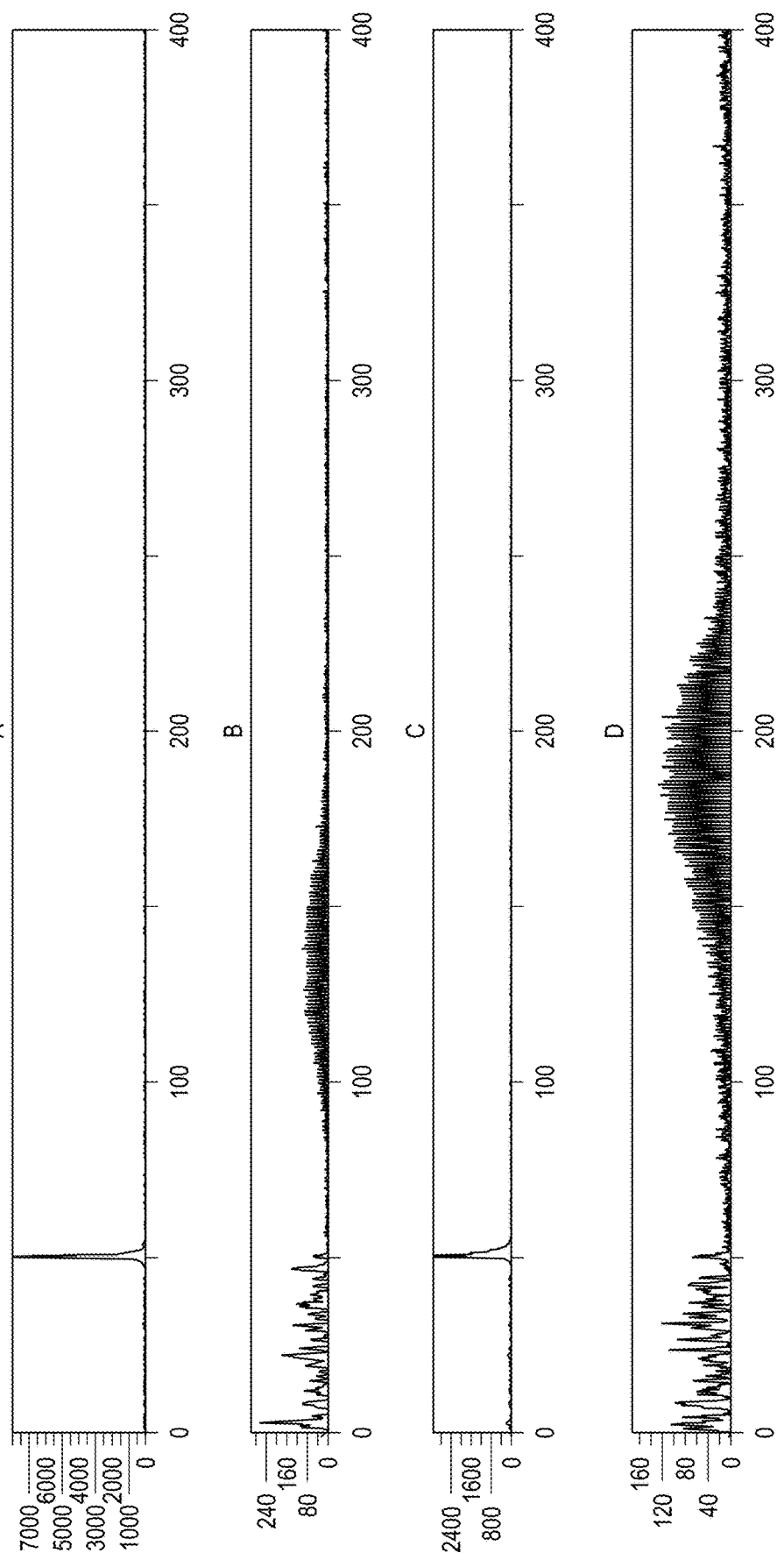
FIG. 6 shows that poly(A) tailing activity from soluble or immobilized SNAP-tagged poly(A) polymerase (PAP). The following four reaction samples (from top to bottom) were analyzed by CE technique: Sample 1, 45-mer RNA oligo substrate without enzymatic treatment; Sample 2, substrate treated with soluble PAP; Sample 3, substrate reacted with PAP immobilized to BG-magnetic beads without $PEG_{750}$-coated; sample 4: substrate reacted with PAP immobilized to $PEG_{750}$-coated BG magnetic beads. Sample 2 and Sample 4 displayed poly(A) tailing activity.

Poly(A) tailing reactions were performed using the soluble and immobilized poly(A) polymerase according to the protocols described in Example 1. The data shown in FIG. 6 demonstrate that SNAP-tagged poly(A) polymerase immobilized to $PEG_{750}$-coated magnetic beads displayed poly(A) tailing activity on a 45-mer RNA oligo whereas the same fusion protein immobilized to magnetic beads without $PEG_{750}$ coating displayed little, if any, detectable poly(A) tailing.

Example 3: Immobilized T4 DNA Ligase Displays Stability Including Thermostability

Example 3A. T4 DNA Ligase Immobilization on Magnetic Beads and Stability Assays This example provides immobilization of SNAP-tagged T4 DNA Ligase to BG-magnetic Beads and validation of storage stability at −20° C. and 25° C.

HS-T4 DNA Ligase protein was immobilized to BG-Magnetic-Beads by mixing 100 µg protein per 400 µl of 25% (V/V) bead slurry at 4° C. overnight in 1×PBS buffer containing 1 mM DTT, followed by extensive wash (8×). The resulting immobilized enzyme was termed BG-HS-T4 DNA Ligase and stored at −20° C. or 25° C. for 7 days. Activity testing was performed according to the Determination of the Unit Activity of T4 DNA Ligase by Capillary Electrophoresis (CE) activity assay (One unit is defined as the amount of enzyme required to give 40% to 70% (55%±15%) ligation of 0.12 µM of synthesized double-stranded DNA oligos with Hind III ends in 20 minutes at 16° C.

Figure 7:
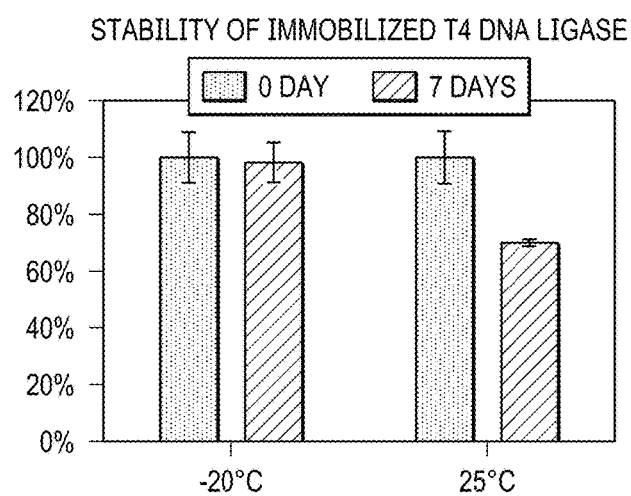
FIG. 7 shows relative activity of T4 DNA ligase immobilized on magnetic beads stored at –20° C. or 25° C. over a period of 7 days. The activity at day 1 is normalized to 100%.

Results are shown in FIG. 7. No detectable decrease in enzyme activity was observed at −20° C. and an approximately 30% reduction in ligase activity at 25° C. during the storage period.

Example 3B. T4 DNA Ligase Immobilization on Agarose Beads

This example demonstrates that immobilization can improve thermostability of SNAP-tagged T4 DNA ligase conjugated to BG-Agarose beads (HS-T4 DNA Ligase Agarose) compared to free SNAP-tagged T4 DNA ligase (HS-T4 DNA Ligase) or untagged T4 DNA ligase (NEB M0202). HS-T4 DNA Ligase protein was immobilized to SNAP-Capture Pull-Down Resin (a highly crosslinked agarose, NEB S9144), termed BG-Agarose, by mixing 100 µg protein per 100 µl of 50% bead slurry at 4° C. overnight in 1×PBS buffer containing 1 mM DTT, followed by extensive wash. The resulting immobilized enzyme was termed HS-T4 DNA Ligase Agarose. Each immobilized enzyme master mixture was made by mixing 32 µL of HS-T4 DNA Ligase Agarose, 20 µL of 10× T4 DNA Ligase Reaction Buffer and 74.64 µL of H2O; Two types of soluble enzyme master mixtures were made by mixing 8 µL of T4 DNA Ligase (NEB M0202) or HS-T4 DNA Ligase, 20 µL of 10× T4 DNA Ligase Reaction Buffer and 98.64 µL of $H_2O$.

Example 3C. Comparison of Ligase Activity of Soluble and Immobilized Ligases

A FAM-labeled DNA duplex was formed by annealing synthetic oligomer, Gene32FAM-fw3'A,/56-FAMN/CA TGG TGA TTA CGA TTC TTG CCC AGT ATG TCA ATA CAT CAG TAA AAA TA (SEQ ID NO:1) and Gene32-rv5'p,/5Phos/AT TTT TAC TGA TGT ATT GAC ATA CTG GGC AAG AAT CGT AAT CAC CATG (SEQ ID NO:2). A DNA substrate mixture was prepared by mixing 60 µL of 10 µM 5TAM-labeled DNA duplex with 3'A and 160.08 µL of 15 µM TA-Adaptor possessing a 3'T, 5'75Phos/GAT CGG AAG AGC ACA CGT CTG AAC TCC AGT C/ideoxyu/A CAC TCT TTC CCT ACA CGA CGC TCT TCC GAT CT-3' (SEQ ID NO:3).

Figure 8:
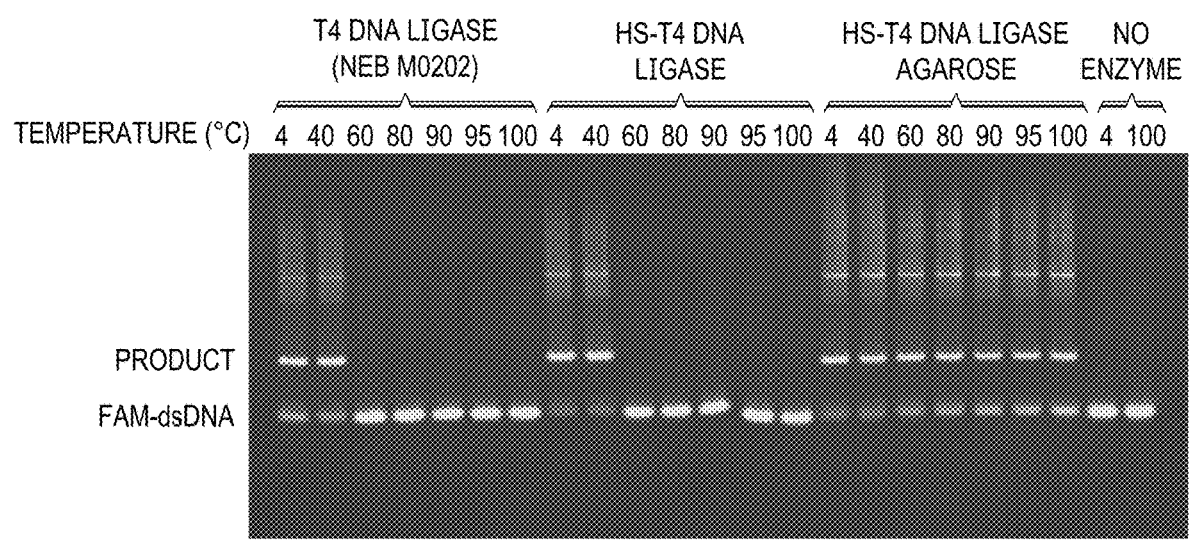
FIG. 8 shows that T4 DNA ligase immobilized on agarose beads is more thermostable than two soluble T4 DNA ligases. Heat treatment was conducted with two soluble T4 DNA Ligases, untagged T4 DNA Ligase (NEB M0202) and SNAP-tagged T4 DNA Ligase (HS-T4 DNA Ligase), and immobilized T4 DNA ligase (HS-T4 DNA Ligase-Agarose). Ligase activity was monitored using FMA-labeled synthetic double-stranded DNA (FAM-dsDNA). The substrate/enzyme mixtures were treated at various temperatures (40° C.-100° C.), followed by incubation at 4° C. overnight. Fluorescent gel scanning was used to visualize substrate and ligation products (including the major product, termed Product), as detected in positive controls when the reactions were pre-treated at 4° C. but were absent in the negative controls (NO Enzyme).

For heat treatment, an aliquot of 15.83 µL from an enzyme master mixture was incubated at 4, 40, 60, 80, 90, 95 or 100° C. for 10 min, followed by addition of 9.17 µL of the DNA substrate mixture. All the ligation reactions were carried out at 4° C. overnight in a shaker. The samples were analyzed by electrophoresis on a 12% Tris-Glycine PAGE (Novex/Invitrogen) in 1×TAE Buffer for 2.5 hours at 25 mA (current). Results are shown in FIG. 8. The DNA species possessing FAM probe signal was detected by scanning the PAGE gel with an 488 nm excitation wavelength on Typhoon Imager (GE Healthcare). DNA ligation resulted in formation of new species of larger molecular mass, absent in the control reactions without ligase (No Enzyme). Both untagged T4 DNA ligase and soluble HS-T4 DNA Ligase showed no detectable ligase activity after treatment in the temperature range of 60-100° C., indicating that soluble form was subjected to irreversible denaturation. In contrast, HS-T4 DNA Ligase immobilized to BG-Agarose beads retained enzymatic activity after treatment in the same range of elevated temperature tested.

Example 3D. Effect of Heat Treatment on Various Soluble and Immobilized Products of T4 DNA Ligases Four types of beads, Agarose (SNAP-Capture Pull-Down Resin, NEB S9144), Chitin, Magnetic beads (Mag), SiMag beads (SiM) were modified to possess benzylguanine ligand, a substrate of SNAP-tag. SNAP-tagged T4 DNA Ligase (HS-T4 DNA Ligase) protein was immobilized to each type of benzylguanine-functionalized beads. A typical immobilization reaction was performed by mixing 100 µg protein with an Agarose bead slurry at 4° C. overnight, followed by extensive wash. The resulting immobilized enzyme was termed Ligase-Agarose, Ligase-Chitin, Ligase-Mag and Ligase-SiM, respectively. Ligation reactions were set up by mixing the following components in a final volume of 20 µL containing 1× T4 DNA Ligase Reaction Buffer, 0.5 µM FAM-labeled DNA duplex, 3.75 µM adaptor, and 1 µL of immobilized HS-T4 DNA Ligase or HS-T4 DNA Ligase (HS-Ligase) or T4 DNA Ligase (Ligase, NEB M0202S). The reaction mixtures were incubated for 30 min at 4° C.

Figure 9:
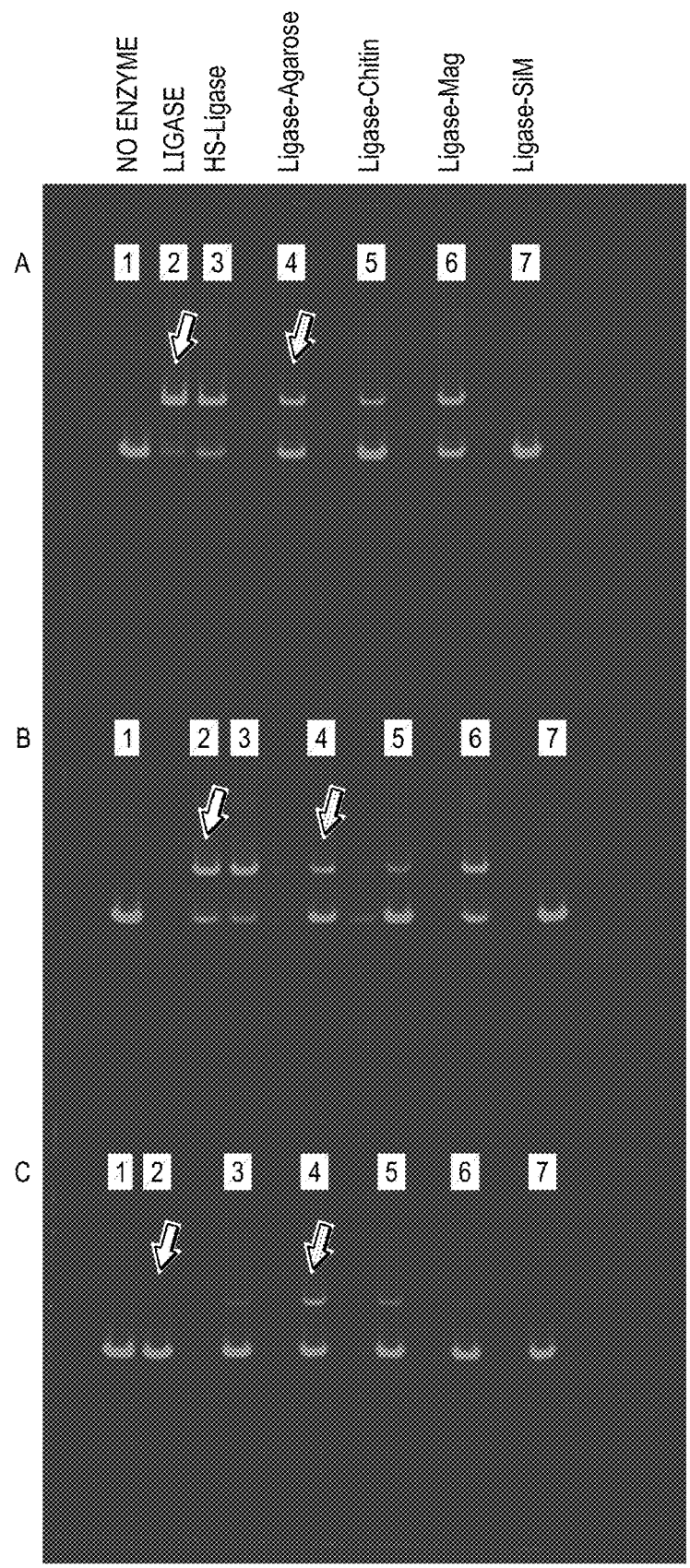
FIG. 9 shows that SNAP-tagged T4 DNA Ligase immobilized onto agarose beads displayed ligase activity after heat treatment at 45° C. for 30 min but the soluble form showed little or no ligase activity under the same conditions. Aliquots of HS-T4 DNA Ligase conjugated to BG-Agarose beads were incubated for 30 min at 4° C. (A), 37° C. (B) or 45° C. (C), followed by ligation reactions at room temperature (23° C.) for 2 hours. The samples (in the same order) were loaded onto three PAGE gels for electrophoretic separation, followed by fluorescent gel scanning. 1, No Enzyme; 2, Ligase (untagged T4 DNA Ligase, NEB M0202); 3, HS-Ligase (SNAP-tagged T4 DNA Ligase); 4, Ligase-Agarose; 5, Ligase-Chitin; 6, Ligase-Mag; 7, Ligase-SiM. Arrows indicate the expected positions of ligation product for soluble T4 DNA Ligase (arrows in lane 2) or Ligase-Agarose (arrows in lane 4).

(A), 37° C. (B) or 45° C. (C). Subsequently, all the reaction mixtures were incubated for 2 hours at 23° C. for DNA ligation to proceed. The samples were analyzed by electrophoresis on a 12% Tris-Glycine PAGE (Novex/Invitrogen) in 1×TAE Buffer for 2.5 hours at 25 mA (current). The DNA species possessing FAM signal was visualized by scanning the PAGE gel with an 488 nm excitation wavelength on Typhoon Imager (GE Healthcare). Results are shown in FIG. 9. DNA ligation resulted in formation of a product of higher molecular mass, which is absent in the control reactions without ligase (No Enzyme).

All ligase-containing reactions except for Ligase-SiM showed ligase activity after treatment at 4° C. (FIG. 9A) or 37° C. (FIG. 9B) for 30 min. FIG. 9C shows that after heat treatment at 45° C. HS-T4 DNA Ligase immobilized to BG-Agarose beads retained higher enzymatic activity compared to the other immobilized ligase products. Both untagged T4 DNA ligase (Ligase) and soluble HS-T4 DNA Ligase (HS-Ligase), however, showed no or residual ligase activity after treatment at 45° C. for 30 min, indicating that these soluble form ligases was subjected to irreversible denaturation.

Figure 10:
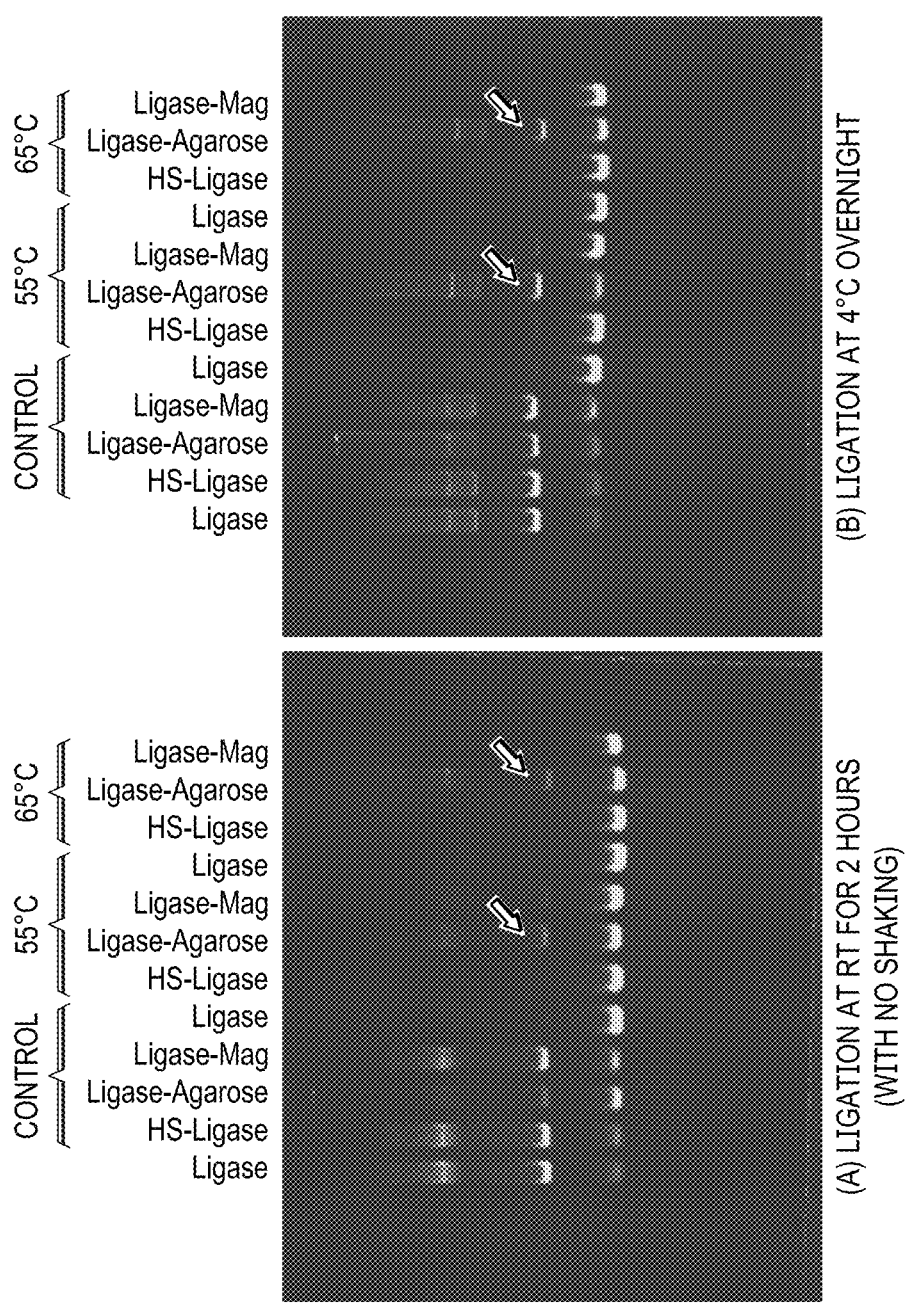
FIG. 10 shows that SNAP-tagged T4 DNA Ligase immobilized onto agarose beads displayed more ligase activity after heat treatment at 55° C. or 65° C. than the soluble form which had little or no ligase activity under the same conditions. DNA ligation was monitored using a fluorophore (FAM)-labeled DNA substrate. The reactions were incubated for 10 min at 4° C., 55° C. or 65° C., followed by ligation reactions at 23° C. for 2 hours (FIG. 10A) or at 4° C. overnight (FIG. 10B). The samples were electrophoresed on PAGE gels, followed by fluorescent gel scanning Ligase, untagged T4 DNA Ligase, NEB M0202; HS-Ligase, SNAP-tagged T4 DNA Ligase; Ligase-Agarose, HS-T4 DNA Ligase immobilized to BG-Agarose Beads; Ligase-Mag, HS-T4 DNA Ligase conjugated to BG-Magnetic Beads. Arrows indicate the major ligation product from the reactions with Ligase-Agarose.

Example 3E. Effect of Heat Treatment on Various Soluble and Immobilized Products of T4 DNA Ligases SNAP-tagged T4 DNA Ligase (HS-T4 DNA Ligase) protein was immobilized to BG-Agarose Beads (SNAP-Capture Pull-Down Resin, NEB 59144) and BG-Magnetic Beads (Mag, 1 µm) functionalized with benzylguanine ligand. The resulting immobilized enzyme was termed Ligase-Agarose and Ligase-Mag, respectively. Ligation reactions were set up by mixing the following components in a final volume of 20 µL containing 1×T4 DNA Ligase Reaction Buffer, 0.5 µM FAM-labeled DNA duplex, 3.75 µM adaptor, and 1 µL of immobilized HS-T4 DNA Ligase or HS-T4 DNA Ligase (HS-Ligase) or T4 DNA Ligase (Ligase, NEB M0202S). The reaction mixtures were incubated for 10 min at 4° C., 55° C. (B) or 65° C. Subsequently, the reaction mixtures were incubated either at 23° C. for 2 hours (FIG. 10A) or at 4° C. overnight (FIG. 10B). The samples were electrophoresed on a 12% Tris-Glycine PAGE (Novex/Invitrogen) in 1×TAE Buffer for 2 hours at 25 mA/gel. The DNA species possessing FAM probe were visualized by scanning the PAGE gel with an 488 nm excitation wavelength on Typhoon Imager (GE Healthcare). Results are shown in FIG. 10. All positive control reactions (4° C.) displayed ligase activity. Untagged T4 DNA ligase (Ligase) and soluble HS-T4 DNA Ligase (HS-Ligase) as well as HS-T4 DNA Ligase immobilized onto Magnetic Beads (Ligase-Mag) showed no or residual ligase activity after treatment at 55° C. or 65° C. In contrast, HS-T4 DNA Ligase immobilized to BG-Agarose Beads exhibited similar enzymatic activity for each series of ligation reactions when pre-treated at 4° C., 55° C. or 65° C., indicating that immobilization to BG-Agarose Beads improved heat resistance of T4 DNA Ligase.

Example 3F. Reusing T4 DNA Ligase to Incorporate Unique Molecular Identifiers (UMIs)

For next-generation sequencing, barcoding is an effective and commonly used approach in multiplexed deep sequencing experiments. During the demultiplexing step, identification of UMIs (barcodes) enables calling and quantification of the individual libraries which are pooled for a single sequencing run. Furthermore, UMIs are increasingly used to track nucleic acids from individual cells and to quantitatively assess their clonal contributions over time. This example provides a workflow for efficiently producing libraries with UMIs that reuses immobilized enzymes.

A typical library preparation protocol may consist of (a) repairing the ends of the members of a population of nucleic acids, (b) A/dA-tailing repaired members of the population, (c) ligating adapters to A/dA tailed members of the population, and (d) bead purification of adapter-tagged members of the population. Using immobilized enzymes in accordance with this example obviates the need for bead purification and allows enzymes to be reused in subsequent cycles of library preparation.

In each cycle, a nucleic acid library may be ligated to an adapter with a bar code using immobilized enzymes in accordance with Example 4E to produce an adapter tagged library. Immobilized enzyme beads (IM-Poly(A) polymerase and IM-ligase) are extensively washed, for example, at least 5 times to remove residual barcoded adaptor, as demonstrated in the experiment below and retained for reuse in the next cycle. A wash step can be incorporated to wash away residual bar-coded adaptor in each cycle before an adaptor possessing a different barcode is ligated to RNA species from a fresh RNA sample. The number of cycles may be varied, and all resulting adapter-tagged libraries may be pooled for multiplex sequencing.

In this example, a preparation of 300 units of T4 DNA ligase immobilized onto magnetic beads was utilized to perform repeated ligation of two adaptors used for library construction for Nanopore direct RNA sequencing. One of the adaptor sequences was labeled with a 5' FAM probe to detect and quantify the ligation product using capillary electrophoresis. In each reaction cycle, (a) an RNA library and the adapters were added to a vial containing the immobilized ligase and incubated at 25° C. for 10 min; (b) the enzyme-bearing beads were pelleted on magnetic rack; (c) the product-containing supernatant was removed from the vial and transferred for CE analysis; and (d) the pelleted beads were washed 5 times in conjunction with microcentrifugation in preparation for the next adaptor ligation cycle.

Figure 11:
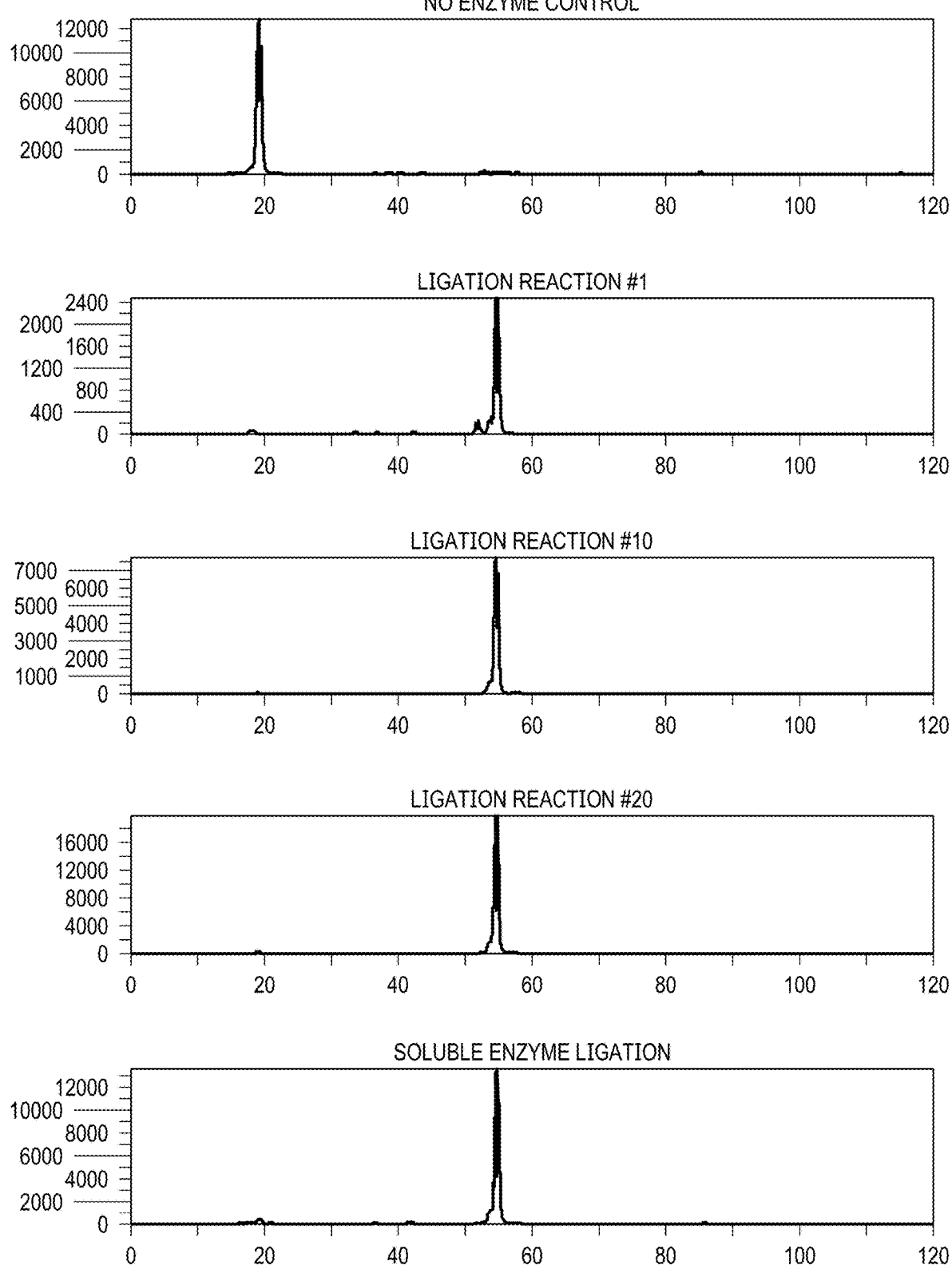
FIG. 11 shows that immobilized enzymes can be reused for consecutive reactions. Data from reactions #1, #10, and #20 of twenty consecutive ligation reactions catalyzed by a single preparation of immobilized T4 DNA ligase. Performance over these twenty reactions matches the results observed in a single reaction with soluble T4 DNA ligase.

Results are shown in FIG. 11 and demonstrate efficient ligation in 20 consecutive ligation reactions, which is indicative of reliability and reproducibility of immobilized T4 DNA ligase. In the control, soluble T4 DNA ligase was used to carry out a single ligation reaction for the same adaptor substrates.

Example 4: Library Preparation Using Soluble and Immobilized Enzymes and Nanopore Direct RNA Sequencing Nanopore direct RNA sequencing was performed using libraries prepared according to one of the five methods described in this example and illustrated in FIG. 1A-E. Total RNA from *Listeria monocytogenes* was extracted using NEB Monarch Total RNA Miniprep Kit (NEB #T2010) and DNase I pack (NEB #T2019L) according the protocols of the manufacturer. The concentration of purified total RNA was measured using Invitrogen Qubit™ RNA High-sensitivity Assay Kit (cat. Number: Q32852).

Details of RNA library preparation for each approach are discussed below. In all cases in this Example 4, sequencing preparation began with 500 ng of each RNA as recommended by Oxford Nanopore Technologies. For the libraries prepared with soluble enzyme with bead purification, Nanopore's bead purification protocol was adopted. After bead purification 20 µL of the resulting RNA library was mixed with 17.5 µL of nuclease-free water and 37.5 µL of RNA running buffer (provided by ONT) to a final volume of 75 µL before loading into a flow cell for direct RNA sequencing. For the libraries prepared with soluble enzyme without bead purification, and immobilized enzymes, a portion of each 40 µL RNA library was supplemented with nuclease-free water to 37.5 µL, and mixed with 37.5 µL RNA running buffer to a final volume of 75 µL.

Direct RNA sequencing was performed on a MinION® MkIb with R9.4 flow cells. MinKNOW® instrument software (ONT) recorded the nanopore current as each strand of an adaptor-ligated RNA translocated through a nanopore. Albacore 1.2.1 (ONT) was used to perform base-calling. A report that displayed the major data sets was generated for each sequencing. Major parameters, such as direct RNA reads and average read length, were compared.

Example 4A. Soluble Poly(A) Polymerase without Bead Purification (FIG. 1A)

For poly(A) tailing, mix 8 µL quick ligation buffer, 1.2 µL 5 M NaCl solution, 0.5 µL poly(A) polymerase (NEB M0276), and 500 ng total *Listeria monocytogenes* RNA, supplemented with nuclease-free water to 30 µL in a 0.2 mL thin-walled PCR tube. Incubate the reaction at 37° C. for 20 min. Next, for adaptor ligation, add 1.0 µL RT Adaptor (RTA), 6.0 µL RNA Adaptor (RMX) and 3.0 µL T4 DNA ligase (NEB M0202M) to the poly(A) tailed RNA sample to make a final volume of 40 µL. Incubate the reaction at 25° C. for 10 min RNA concentration was measured using the Qubit method after the enzymatic reaction (FIG. 1A). An aliquot of 40 µL RNA sample was used for further library prep as described above.

Example 4B. Sequential Reactions with Soluble Enzymes and Bead Purification (FIG. 1B)

Library preparation according to Example 4A was repeated with the addition of a bead purification step after the enzymatic reactions. Specifically, 40 µL of resuspended NEBNext Sample Purification beads (E7104S) were combined with the adapter ligation reaction (40 µL) and mixed by pipetting and incubated on a Hula mixer (rotator mixer) at room temperature for 5 min. Samples were spun and pelleted on a magnet. Supernatant was pipetted off while pellets were retained on a magnet. Beads were combined with 150 µL of Wash Buffer (WSB) (150 µL) and resuspended by flicking the tubes. Tubes were returned to the magnetic rack to allow beads to pellet and supernatant was removed by pipette. The wash step was repeated and the supernatant was removed. Each pellet was resuspended in 21 µL Elution Buffer by gently flicking the tube after removal from the magnetic rack. Each tube was incubated at room temperature for 10 min to allow the elution of RNA. Beads were then pelleted on a magnet until the eluate was clear and colorless. 21 µL of each eluate was removed and retained in a clean Eppendorf DNA LoBind® tube. 1 µL of RNA was used for concentration measurement using Qubit Assay Kit. Final yield and recovery rate were determined. All 20 µL RNA samples were used for further library prep as described above.

Example 4C. Coupled Reactions with Soluble Poly(A) Polymerase and Bead Purification (FIG. 1C)

For the coupled reactions approach using soluble enzymes, mix 8 µL quick ligation buffer, 1.2 µL 5 M NaCl solution, 0.5 µL poly(A) polymerase (NEB M0276), 500 ng total RNA, 1.0 µL RT Adaptor (RTA), 6.0 µL RNA Adaptor (RMX) and 3.0 µL T4 DNA ligase (NEB M0202M) supplemented with nuclease-free water to 40 µL in a 0.2 mL thin-walled PCR tube. Incubate the reaction at 37° C. for 20 min followed by 25° C. for 10 min to allow the simultaneous poly(A) tailing and adaptor ligation. Sample purification, RNA concentration determination, and further RNA library prep (using all 20 µL) were carried out as described in Example 4B.

Figure 12:
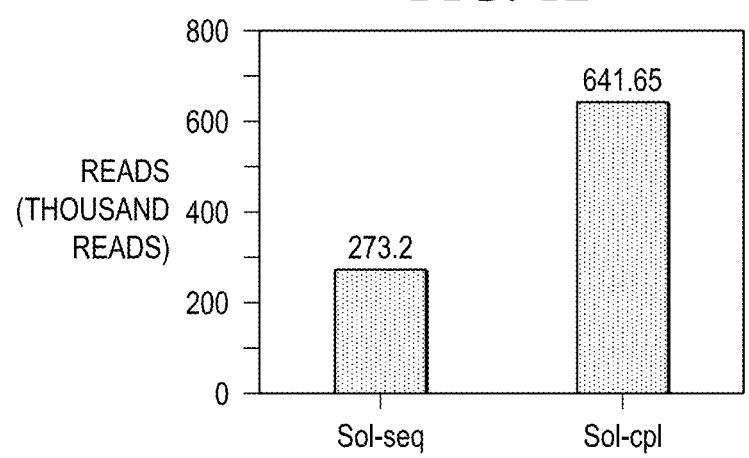
FIG. 12 shows number of direct RNA sequencing reads from libraries prepared by two methods. In the first, labeled Sol-seq, the library was prepared by two sequential steps of poly(A) tailing and adaptor ligation. In the second, labeled Sol-cpl, the library was prepared by carrying out poly(A) tailing and adaptor ligation simultaneously.

Comparison of Nanopore direct RNA sequencing reads. Each library was prepared using soluble enzyme with bead purification by sequential (Sol-seq) and coupled (Sol-cpl) reaction protocols for poly(A) tailing and adaptor ligation. Results are shown in FIG. 12.

Example 4D. Sequential Reactions with Immobilized Enzymes (FIG. 1D)

Figure 13:
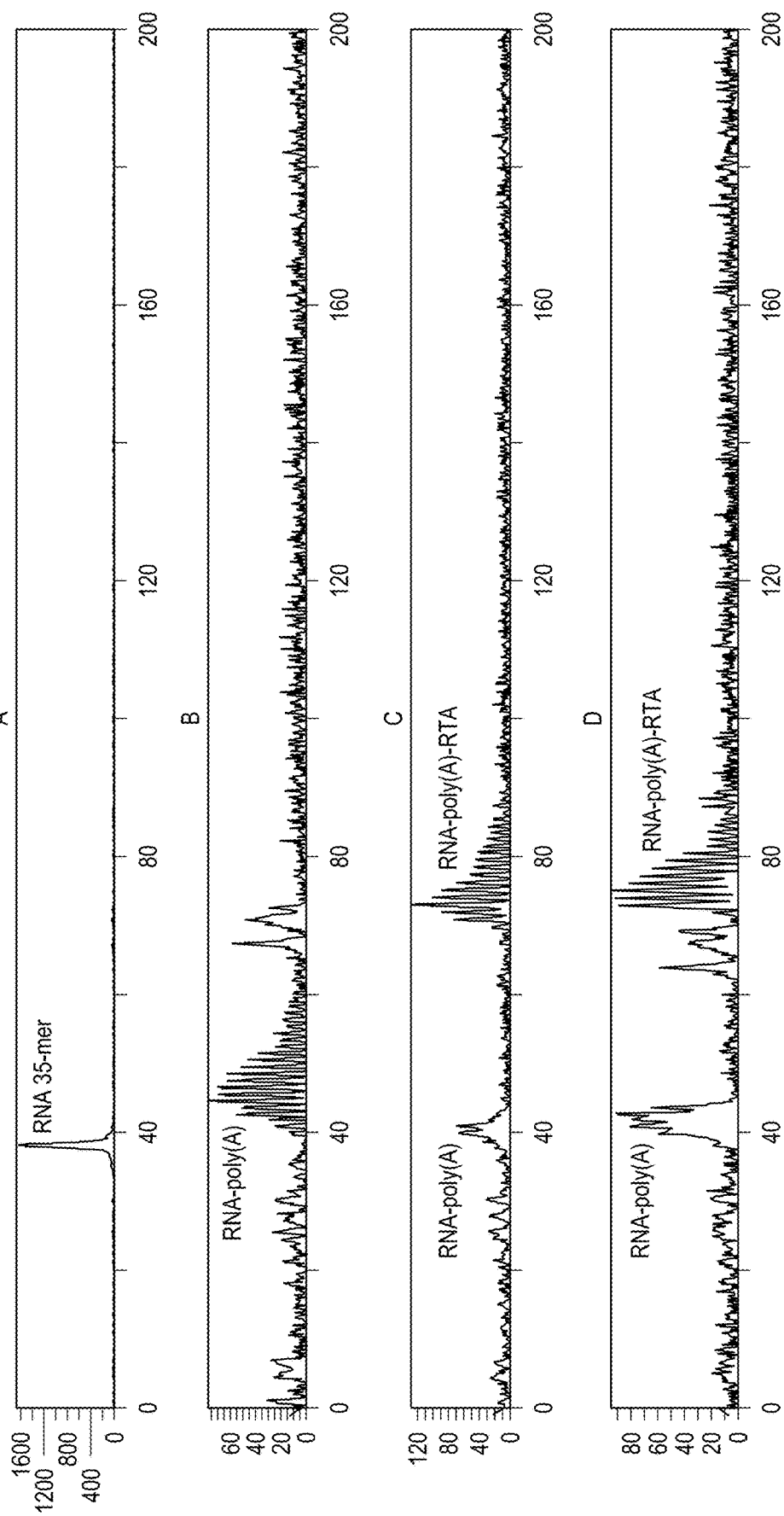
FIG. 13 shows the poly(A) tailing and adaptor ligation activity from immobilized poly(A) polymerase and immobilized T4 DNA Ligase. Four samples were examined by CE (from top to bottom): Sample 1, untreated FAM-labeled RNA substrate showing a distinct peak; sample 2, FAM-labeled RNA substrate treated by immobilized Poly(A) polymerase; Sample 3, Sample 2 treated with immobilized T4 DNA ligase and RTA-poly(dT)$_{15}$; Sample 4, Sample 2 treated with immobilized T4 DNA ligase and RTA-poly(dT)$_{10}$. A bell-shaped peak in Sample 2 represents addition of 3' poly(A) tails of various length to the RNA substrate (Sample 1). Ligation of an RTA adaptor to the poly(A) tailed products generated higher molecular mass products resulting in a shift of the bell-shaped peak to the right.

A model study was conducted by CE analysis of sequential treatment of FAM-labeled RNA oligo (35mer) with immobilized poly(A) polymerase and immobilized T4 DNA ligase. Poly(A) tailing was performed at 37° C. for 20 min after mixing 6 µL nuclease-free water, 1 µL 10× poly(A) polymerase reaction buffer (NEB), 1 µL 10 mM ATP, 0.5 µL RNase inhibitor, 1 µL 1 µM RNA 35-mer oligo (100 nM final concentration) and 0.5 µL immobilized poly(A) polymerase (EXAMPLE 1C). Subsequently, after removal of immobilized PAP ligation was carried out at 25° C. for 10 min with the addition of immobilized T4 DNA Ligase (provided by NEB, 60 units/µL) and RTA-poly(dT)$_{15}$ or RTA-poly(dT)$_{10}$ (300 nM). Positive results were observed by CE analysis of the samples taken from the poly(A) tailing reaction and adaptor ligation reactions (FIG. 13).

An RNA library was also prepared using immobilized enzymes using the same workflow as described in Example 4B above except that the soluble enzymes (i.e. poly(A) polymerase and T4 DNA ligase) were replaced with their immobilized counterparts. Briefly, poly(A) tailing and ligation were carried out sequentially by incubating RNA with 2.5 µL immobilized Poly(A) polymerase at 37° C. for 20 min., removing the beads, incubating the supernatant with 3.0 µL immobilized T4 DNA ligase at 25° C. for 10 min., and removing the beads with immobilized T4 DNA ligase Immobilized enzymes, poly(A) polymerase in the first step and T4 DNA ligase in the second step, were separated from the reaction medium on a magnetic rack and the supernatant containing the products and other soluble components were transferred to a fresh tube for the subsequent reaction. No bead purification was performed after the ligation of RTA and RMX adapters. The RNA concentration in the supernatant was determined using Qubit method. A portion of the 40 µL RNA library was supplemented with nuclease-free water to 37.5 µL, and mixed with 37.5 µL RNA running buffer to a final volume of 75 µL before loading into a flow cell for direct RNA sequencing.

FIG. 14 shows that using immobilized enzymes yielded total reads and sequence length comparable to both soluble enzymes and bead purification, indicating that immobilized enzymes can be used to substitute soluble enzymes in catalyzing poly(A) tailing and adaptor ligation reactions. In addition, immobilized enzymes generated many more sequence reads than the soluble enzyme protocol incorporating no bead purification. Thus, removal of the enzyme components from the RNA library appears to be sufficient for generation of high sequence reads in nanopore sequencing presumably by avoiding clogging of nanopores by enzyme molecules. The soluble enzyme protocol without bead purification yielded fewer reads, suggesting that proteins or other components in the reaction mixture may cause nanopore fouling. Soluble enzyme protocol with bead purification also displayed fewer reads probably due to impurities as the result of bead purification.

Example 4E. Coupled Reactions with Immobilized Enzymes (FIG. 1E)

The sequential poly(A) tailing and ligation steps (shown in Example 4D) were combined into a single, coupled reaction as shown in FIG. 1E. Poly(A) tailing and ligation were carried out by using 2.5 µL immobilized Poly(A) polymerase and 3.0 µL immobilized T4 DNA ligase together at 37° C. for 20 min followed by 25° C. incubation for 10 min. The immobilized enzyme beads were separated from the reaction medium on magnetic rack and the supernatant containing the products and other soluble components were transferred to a fresh tube. A library was also prepared using the sequential reaction protocol with immobilized enzymes described in EXAMPLE 4D.

The RNA concentration in the resulting libraries was determined using Qubit method. The same amount of RNA from each library was used to prepare the sequencing mixtures supplemented with nuclease-free water to a volume of 37.5 µL and another 37.5 µL of RNA running buffer (RRB) were used to prepare 75 µL sample for RNA sequencing according to Example 2D. Direct RNA sequencing for both sequential (Example 2C) and coupled reaction (this example) were performed on a MinION® MkIb with R9.4 flow cells as introduced before.

Figure 15:
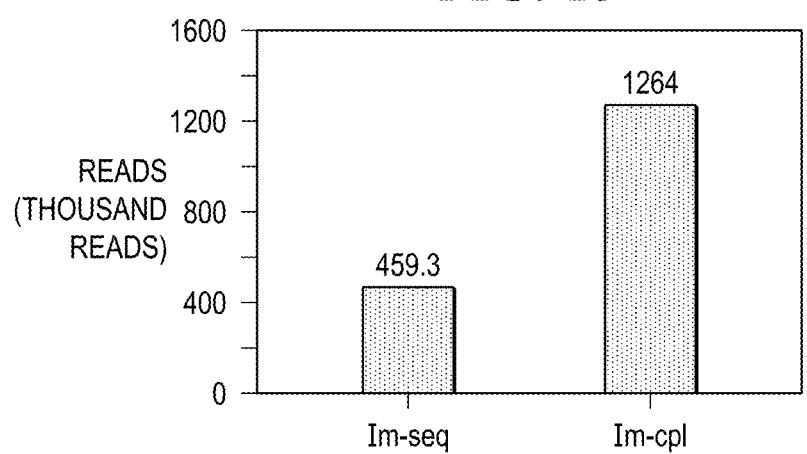
FIG. 15 shows total sequence reads from Nanopore direct RNA sequencing of RNA libraries constructed with 500 ng input RNA using immobilized enzymes without AMPure® bead purification following either sequential reaction protocol (Im-seq) or coupled reaction protocol (Im-cpl). After enzymatic treatment enzyme-conjugated beads were pelleted on a magnetic rack and the supernatants were transferred to a fresh tube. 105 ng of total RNA from each library was mixed with the solution provided by ONT before loading onto MinION® R9.1.4 flow cells for direct RNA sequencing.

Results shown in FIG. 15 contrast the number of sequencing read from the coupled reaction protocol to that of the sequential reaction protocol using immobilized enzymes. The library prepared using a sequential reaction strategy (Example 4D) with an RNA sequencing input of 105 ng of RNA yielded 459 K reads, which is comparable to the results presented in Example 4C with final yield of 488.5 K reads from 164.4 ng of RNA input. However, the library prepared in this Example using a coupled reaction protocol with immobilized enzymes with similar amount of RNA input produced almost a 3-fold increase in RNA sequencing reads compared to a sequential reaction protocol using immobilized enzymes.

Example 4F. Coupled Reactions with Co-Immobilized Enzymes $O^6$-benzylguainine (BG) functionalized magnetic beads coated with $PEG_{750}$ (100 µL of a 25% (v/v) slurry) were used for enzyme co-immobilization. Poly(A) polymerase—SNAP fusion protein and T4 DNA ligase—SNAP fusion protein (12.5 µg of each) were dissolved in 125 µL buffer (1×PBS with 300 mM NaCl), combined with the washed BG beads, and incubated at 4° C. overnight to immobilize the fusion protein on the beads, according to the procedure described in EXAMPLE 1C. The co-immobilized beads were washed with the same buffer 8 times to remove any unbound enzyme molecules. Diluent A buffer without BSA (NEB) with 100 mM NaCl was used to resuspend the beads with immobilized fusion protein for storage at −80° C.

Figure 16A:
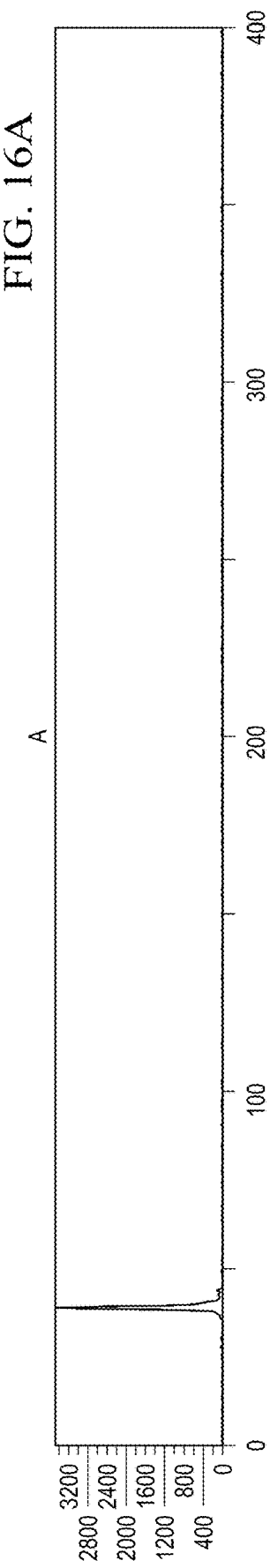
FIG. 16A-B shows that co-immobilized enzymes displayed both poly(A) polymerase activity and T4 DNA ligase activity.
Figure 16A:
Figure 16B:
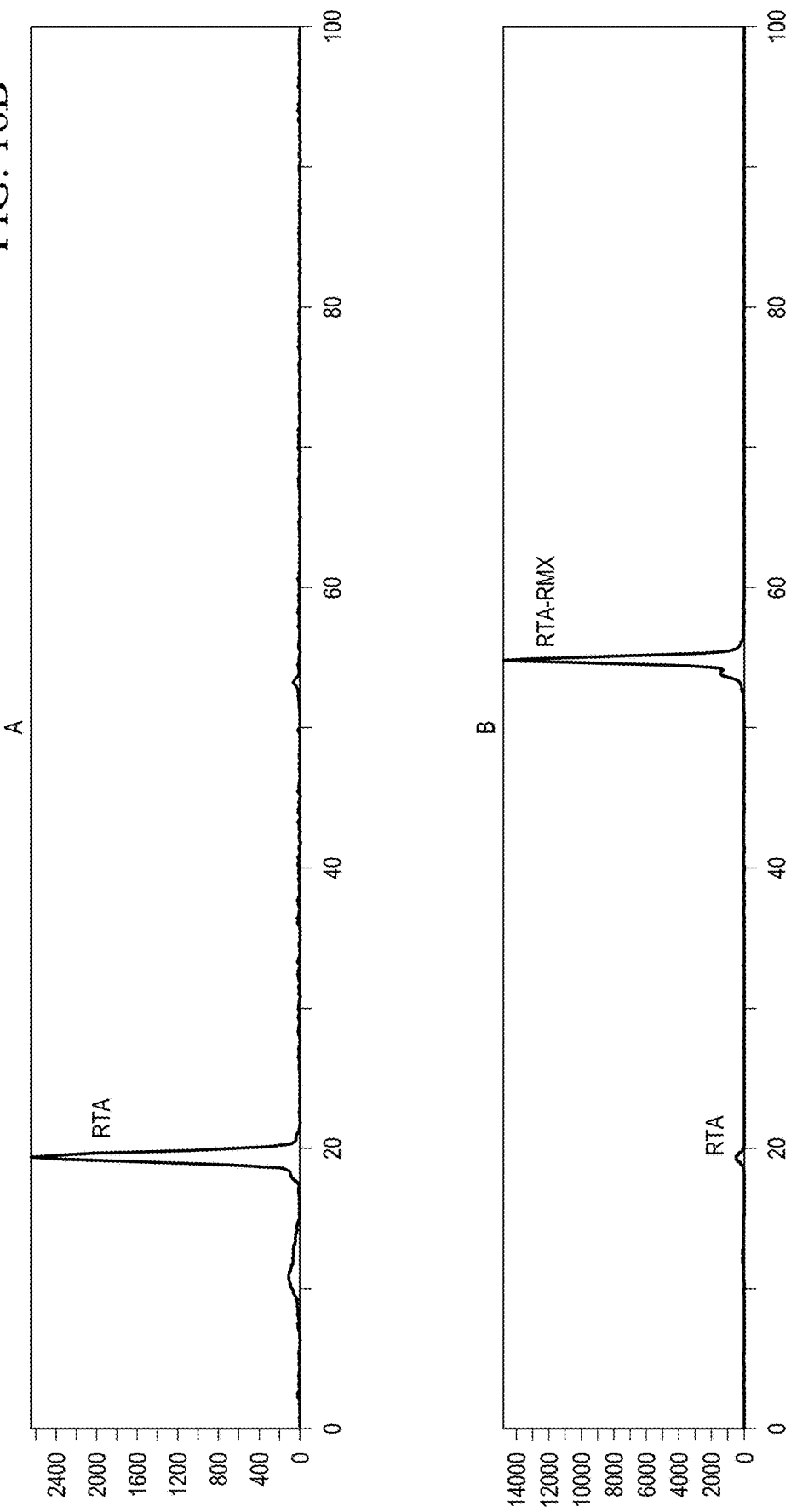

Poly(A) tailing and adaptor ligation activities were measured for the bead sample co-immobilized with poly(A) polymerase and T4 DNA ligase. 5 µL of the co-immobilized enzyme bead mixture were used to replace 2.5 µL immobilized poly(A) polymerase and 3 µL immobilized T4 DNA ligase in each activity assay. The co-immobilized enzymes displayed both poly(A) polymerase activity (FIG. 16A) and T4 DNA ligase activity (FIG. 16B).

Example 5: Automated Library Construction and Sequencing

Figure 17:
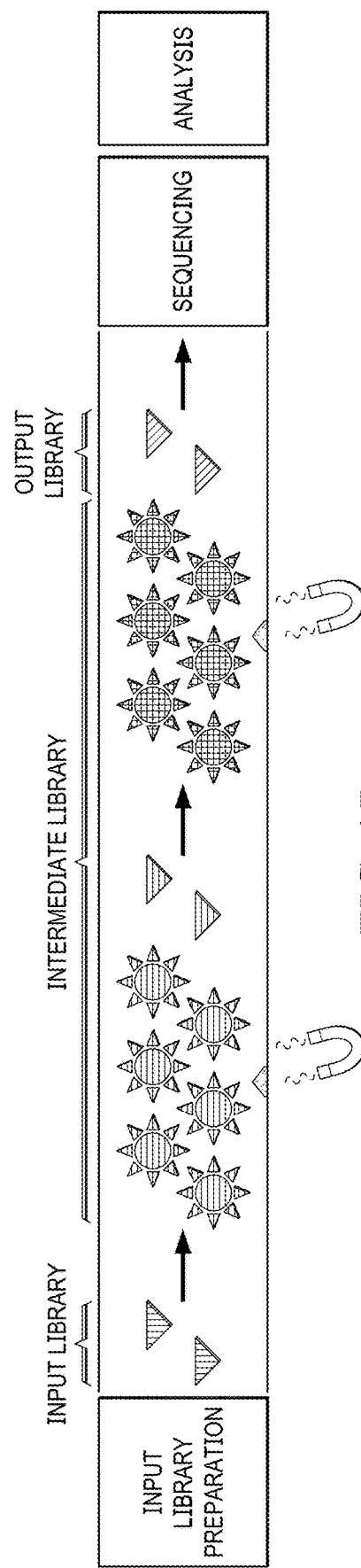
FIG. 17 shows an example of fully automated Nanopore sequencing workflow which includes library construction catalyzed by immobilized enzymes.

While next-generation sequencing (NGS) has greatly advancing biological research and clinical diagnostics, the process would benefit from automation from library construction to sequencing libraries and data analysis. The preceding examples demonstrate that application of immobilized enzymes in multi-reaction library construction workflows avoids bead based nucleic acid purification which may cause sample loss and bias in fragment distribution. Combining the single-reaction preparation of Example 4 with NGS (e.g., using robotics and/or microfluidics) advances automation in sequencing. Specifically, otherwise cumbersome steps of adding adapters to nucleic acid libraries to be sequenced may be in a single reaction vessel and fed directly into sequencing platforms. The concomitant reduction in handling will reduce error rates and variations in high-throughput research and clinical application of Nanopore and other NGS technologies (FIG. 17).

As shown, magnetic beads bearing enzymes are positioned in proper enclosed chamber and tunnel to process an input or intermediate library. There is no extra purification step required for separation of the enzymes and the resulting products, between or after enzymatic reaction steps. The input library can be produced by a method, for example, RNA extraction, that incorporates a properly designed automated workflow. An output library can be properly formulated for direct sequencing on a nanopore sequencing device, i.e. flow cell, such as currently available R9.4.1. or R10. Ultimately, this workflow is linked to locally based or cloud-based computer software to provide a fully automated sequencing solution.

Example 6: Direct RNA Sequencing with Low Input RNA is Possible when Immobilized Enzymes are Used in Library Prep All sequencing reads using the libraries described in Example 4 were performed with 500 ng of RNA as suggested by Oxford Nanopore Technologies. This example demonstrates construction and successful sequencing of duplicate libraries from a lower initial input (100 ng) of *Listeria monocytogenes* RNA using either a sequential or coupled reaction protocol with immobilized poly(A) polymerase and T4 DNA Ligase. For sequential reaction protocol, 3 µL quick ligation buffer, 0.45 µL 5 M NaCl solution, 1.5 µL immobilized poly(A) polymerase, and 100 ng total RNA, supplemented with nuclease-free water to 10 µL were mixed in a 0.2 mL thin-walled PCR tube and incubated at 37° C. for 20 min for poly(A) tailing. After immobilized poly(A) polymerase beads were removed by placing the tube on the magnetic rack, 0.5 µL RT Adaptor (RTA), 3.0 µL RNA Adaptor (RMX) and 1.5 µL immobilized T4 DNA ligase were added to the poly(A) tailed RNA sample to yield a final volume of 15 µL. This mixture was incubated at 25° C. for 10 min for adaptor ligation. The immobilized ligase was removed using the magnet. For the coupled reaction protocol, the same amounts of enzymes and buffer were utilized as disclosed above (except that all the components were combined in a single tube). The mixtures were incubated at 37° C. for 20 min and 25° C. for 10 min, consecutively, and both immobilized enzymes were removed in a single step on the magnetic rack. The RNA yields of the prepared libraries were determined by high sensitivity RNA Qubit assay.

Figure 18A:
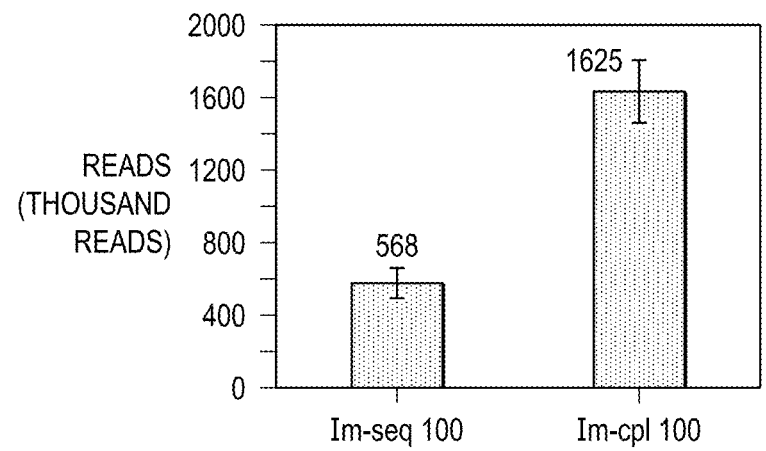
FIG. 18A-B shows the number of Nanopore RNA sequencing reads obtained with low-input RNA libraries prepared with immobilized enzymes.

With the initial RNA input of 100 ng, the sequential and coupled reaction methods resulted in recovery of an average of 38 ng and 83 ng, respectively, from duplicate libraries. Thus, the recovery rate for RNA library prep using the coupled reaction protocol is 83% of the initial input, much higher than that of the sequential reaction protocol (FIG. 18A). The results also suggest that a coupled reaction process generates more reads compared to the sequential reaction. In addition, a sequential reaction generates 568 K reads on average, higher than that obtained from the protocol using soluble enzymes with bead purification. The results demonstrate that low input RNA library construction can be achieved by using both sequential and coupled reaction protocols with immobilized enzymes (FIG. 18A).

Figure 18B:
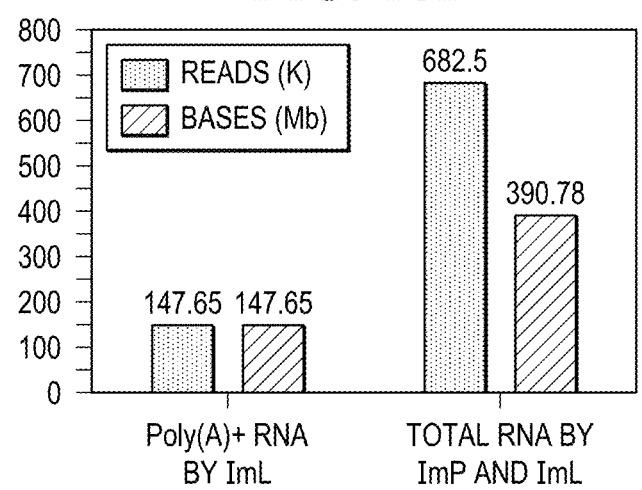

Similar results were obtained with library construction from a low initial input mammalian human brain RNA (100 ng). FIG. 18B shows direct RNA sequencing of low input of poly(A) tailed human RNA (100 ng PolyA+RNA) prepared by ligation to RTA and RMX adaptors with immobilized T4 DNA Ligase (ImL) Furthermore, total mammalian RNA library (100 ng input), prepared with immobilized poly(A) polymerase and immobilized T4 DNA ligase (ImP and ImL) using the coupled reaction protocol described above in this example, was successfully used for direct RNA sequencing.

Example 7: Metrics of the Ont Direct RNA-Seq Datasets from Various Library Preparation Protocols Duplicate libraries using each of the five RNA library preparation protocols were made with 500 ng input RNA extracted from *Listeria monocytogenes* (ATCC 1115) culture. The final volume for the enzymatic reactions was 40 µl prior to bead purification; for soluble enzyme protocols, Sol-seq and Sol-cpl, each RNA library was further purified with RNA binding beads and eluted in 20 µl volume. For immobilized enzyme protocols enzyme removal was performed without purification using RNA binding beads prior to use of a fraction of the library sample for Nanopore direct RNA sequencing. Results are shown in TABLE 1.

TABLE 1

| | 500 ng input libraries | | | | | | | | | |
|---|---|---|---|---|---|---|---|---|---|---|
| | Sol-seq | | | | Sol-cpl | | | | Im-seq | |
| | | | | | Replicate | | | | | |
| | R1 | R2 | Avg | Std | R1 | R2 | Avg | Std | R1 | R2 |
| | FAM9 | FAM9 | | | FAM9 | FAN2 | | | FAN2 | FAN2 |
| | 6082 | 4718 | | | 4789 | 3186 | | | 7746 | 7699 |
| Recovery rate | 29% | 39% | 34% | | 34% | 34% | 34% | | 31% | 47% |
| Loading (ng) | 176 | 197 | 186 | | 196 | 222 | 209 | | 88 | 116 |

TABLE 1-continued

|  |  |  |  |  |  |  |  |  |  |  |
|---|---|---|---|---|---|---|---|---|---|---|
| Loading (μL) | 20 | 20 |  |  | 20 | 20 |  | 20 | 20 |  |
| Reads generated (K) | 134 | 149 | 141 | 8 | 642 | 757 | 699 | 58 | 903 | 798 |
| Bases generated (Mb) | 136 | 168 | 152 | 16 | 681 | 816 | 748 | 68 | 836 | 737 |
| Estimated generated (Mb) | 157 | 200 | 178 | 21 | 829 | 962 | 895 | 66 | 1030 | 896 |
| Bases/Estimated | 0.86 | 0.84 | 0.85 |  | 0.82 | 0.85 | 0.84 |  | 0.81 | 0.82 |
| Run Length (hr) | 18 | 22 | 20 |  | 45 | 53 | 49 |  | 40 | 40 |

| | 500 ng input libraries | | | | | | | | |
|---|---|---|---|---|---|---|---|---|---|
| | Im-seq | | Im-cpl | | | | Sol w/o BP | | |
| | | | Replicate | | | | | | |
| | Avg | Std | R1 | R2 | Avg | Std | R1 | R2 | Avg | Std |
| Recovery rate | 39% |  | FAM9 4697 100% | FAN0 3228 117% | 108% |  | FAL6 8474 | FAL7 0280 |  |  |
| Loading (ng) | 102 |  | 176 | 197 | 186 |  |  |  |  |  |
| Loading (μL) |  |  | 11 | 15.6 |  |  |  |  |  |  |
| Reads generated (K) | 850 | 52 | 1580 | 1070 | 1325 | 255 | 430 | 226 | 328 | 102 |
| Bases generated (Mb) | 786 | 50 | 1610 | 1120 | 1365 | 245 | 427 | 146 | 286 | 140 |
| Estimated generated (Mb) | 963 | 67 | 2000 | 1390 | 1695 | 305 | 526 | 192 | 359 | 167 |
| Bases/Estimated | 0.82 |  | 0.81 | 0.81 | 0.81 |  | 0.81 | 0.76 | 0.80 |  |
| Run Length (hr) | 40 |  | 72 | 72 | 72 |  | 43 | 21 | 32 |  |

Example 8: Comparison of the Major Metrics of the Ont Direct RNA-Seq Datasets from Various Library Preparation Methods The average of the major metrics from duplicate libraries prepared using each of the five RNA library preparation protocols were analyzed. Each library was made with 500 ng input RNA extracted from *Listeria monocytogenes* (ATCC 1115) culture. The final volume for the enzymatic reactions was 40 μl prior to bead purification; for soluble enzyme protocols, Sol-eq and Sol-cpl, each RNA library was further purified with RNA binding beads and eluted in 20 μl volume. For immobilized enzyme protocols enzyme removal was performed without purification using RNA binding beads prior to use of a fraction of the library sample for Nanopore direct RNA sequencing.

Averages of two replicate runs are shown in TABLE 2.

TABLE 2

| 500 ng input libraries | Sol-seq | Sol-cpl | Im-seq | Im-cpl |
|---|---|---|---|---|
| Recovery rate | 0.34 | 0.34 | 0.39 | 1.08 |
| Loading (ng) | 186.4 | 208.8 | 102.0 | 186.4 |
| Loading (μL) | 20 | 20 | 20 | 13.3 |
| Reads generated (K) | 141.42 | 699.33 | 850.42 | 1325 |
| Bases generated (Mb) | 151.58 | 748.15 | 786.34 | 1365 |
| Estimated generated (Mb) | 178.2 | 895.4 | 963.11 | 1695 |
| Bases/Estimated | 0.85 | 0.84 | 0.82 | 0.81 |
| Run Length (hr) | 20.2 | 48.8 | 40.3 | 72.0 |
| Mean read length (nt) | 1145.3 | 1156.4 | 1065.9 | 1107.9 |
| Median read length (nt) | 1157 | 1028 | 950 | 951 |
| Read length N50 | 1493 | 1520 | 1464 | 1511 |
| Mean read quality | 10.2 | 10.1 | 10.2 | 10.2 |
| Median read quality | 10.4 | 10.2 | 10.4 | 10.3 |
| Mapping | 99.6% | 99.2% | 99.3% | 99.1% |
| Mapped reads | 140.84 | 693.52 | 844.55 | 1313.08 |
| Expected Reads (K)/Library | 141.4 | 699.3 | 1615.8 | 3902.4 |
| Expected bases (Mb)/Library | 151.6 | 748.2 | 1494.0 | 4020.2 |
| Ratio of Expected Reads (K)/Library | 1 | 4.9 | 11.4 | 27.6 |

Example 9: Comparison of Nanopore Direct RNA Sequencing Reads

Duplicate libraries were prepared using the five protocols illustrated in FIG. 1A-E. Each library was made with 500 ng input RNA extracted from *Listeria monocytogenes* (ATCC 1115) culture. For Sol-seq and Sol-cpl, each RNA library was further purified with RNA binding beads prior to Nanopore sequencing. Both immobilized enzyme protocols did not utilize a purification step with RNA-binding beads after enzymatic treatment, and enzyme removal was performed with magnetic rack prior to sequencing. Results are shown in FIG. 19.

Figure 20:
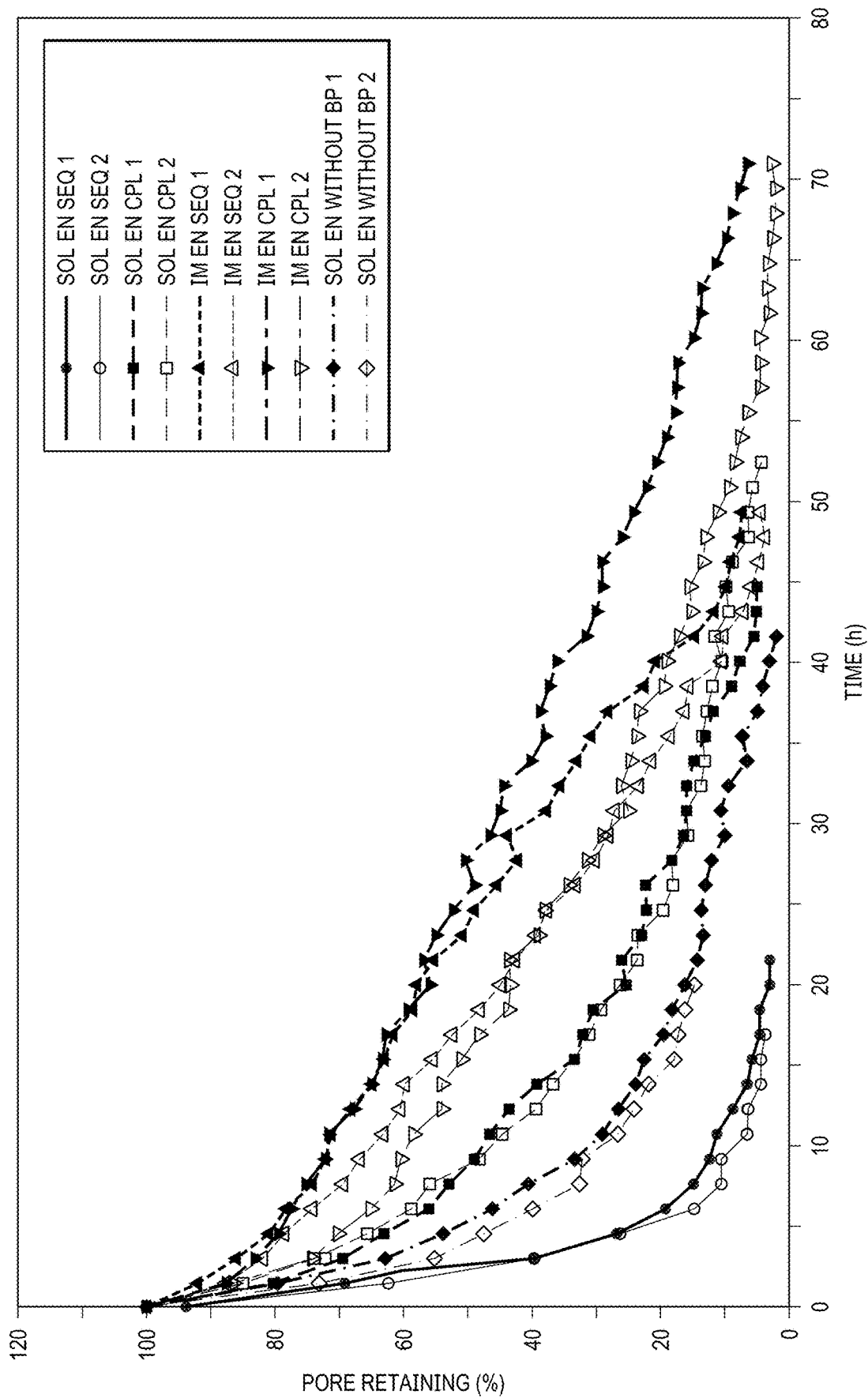
FIG. 20 shows a comparison of functional nanopores over time during direct RNA sequencing runs in ONT flow cells. Duplicate libraries were prepared using each of the five protocols illustrated in FIG. 1A-E and the resulting sequencing reads were displayed in FIG. 19.

Example 10: Reduced Inactivation of Nanopores Using Libraries Prepared with Immobilized Enzymes Data presented in Examples 7-9 demonstrates that bead purification following library preparation with soluble enzymes is associated with a considerable loss of library RNA. Example 13 shows further that omitting a bead purification step (to avoid this loss of RNA) may not be a favorable solution in that the resulting libraries produce substantially fewer sequence reads from the same amount of input RNA compared to the immobilized enzyme protocols. A possible reason for fewer sequence reads from the libraries produced by the soluble enzyme protocol without bead purification is that residual polymerase and/or ligase may occlude nanopores. On the other hand, bead purification may affect library quality due to loss of RNA (or certain RNA types) and may also produce impurity derived from the wash solutions. In this example, the activity of nanopores was monitored over the course of a sequencing run from Min-KNOW® report. Results shown in FIG. 20 demonstrate that more nanopores remain active (upper trace) when the libraries were prepared with immobilized enzymes compared to those prepared with soluble enzymes. For example, after two hours of sequencing, about 90% of the pores processing immobilized enzyme libraries remained active while only about 65% of the pores processing soluble enzyme libraries remained active. At 8 hours, about half of the pores processing immobilized enzyme libraries remained active while only about 10% of the pores processing soluble enzyme libraries remained active. These results demonstrate that the use of immobilized enzymes in library construction can increase nanopore sequencing output, possibly by reducing nanopore fouling.

Figure 21:
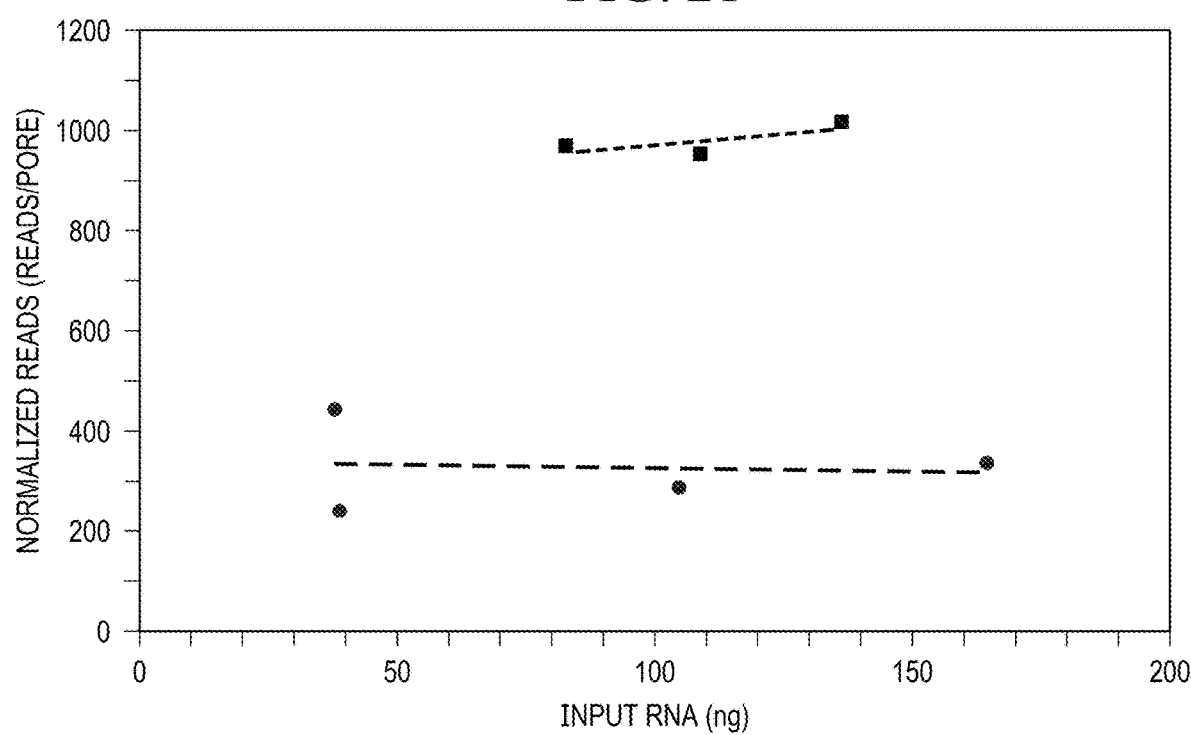
FIG. 21 shows the sequence reads per nanopore from libraries prepared by the coupled reaction method (square dots between 900 and 1100 of normalized reads) in comparison with those from the libraries prepared by the sequential reaction method with immobilized enzymes (circular dots between 200 and 500 of normalized reads). The orange curve aligns the reads/pore data points from three sequencing samples with 83 ng, 109 ng or 136.5 ng loaded on a flow cell. The blue curve aligns the reads/pore data points from four sequencing samples with various amount of RNA (38 ng, 39 ng, 105 ng and 164.4 ng) per flow cell.

The number of reads per pore was also evaluated for the coupled reaction method. Normalized reads shown in FIG. 21 were generated from dividing the reads from sequencing a *Listeria* RNA library by the number of pores.

Three *Listeria* RNA libraries were prepared using the coupled reaction protocol using immobilized enzymes (orange dots). Two low input RNA libraries were prepared in 15 uL following the coupled reaction protocol as described in Example 5, resulting in direct RNA sequencing of 83 ng and 136.5 ng RNA per flow cell, respectively. The third library was prepared as described in Example 4E with 500 ng input RNA in 40 uL and only part of the resulting library (109 ng) was loaded for sequencing.

The number of reads per pore was also examined for a set of four libraries prepared using the sequential reaction protocol using immobilized enzymes (blue dots). Two low input RNA libraries were prepared in 15 uL as described in Example 5, resulting in sequencing 38 ng and 39 ng RNA per flow cell, respectively. Two 500 ng input RNA libraries were made in 40 uL as described in Example 4D and a portion of each resulting library, 105 ng and 164.4 ng, respectively, was used for loading on a flow cell and direct RNA sequencing.

Results indicate that the coupled reaction protocol can generate a significantly higher reads per nanopore compared to the sequential reaction protocol using the same set of immobilized enzymes and conditions (i.e. buffer, total reaction time and volume).

Example 11: DNA Library Construction Workflow for Nanopore Sequencing of Ultra-Long Templates without Bead Purification This example describes a new strategy for preparation of DNA libraries for nanopore DNA sequencing. The current ONT protocol, as depicted in FIG. 26 and Example 13, utilizes a set of four DNA-modifying enzymes to perform end-polishing, dA-tailing and adaptor ligation, in conjunction with bead purification to produce a library for long-read sequencing. Addition of a single 3'A in dA-tailing demands use of PEG in the subsequent adaptor ligation because T/A pairing is inefficient in the absence of PEG or other enhancers. However, use of PEG in conjunction with use of AMPure® beads may not be ideal since PEG can cause DNA compaction onto beads. In addition, application of bead purification can result in shearing of long DNA templates thereby adversely affecting the ability of ultra-long sequence reads by nanopore sequencing.

Figure 22:
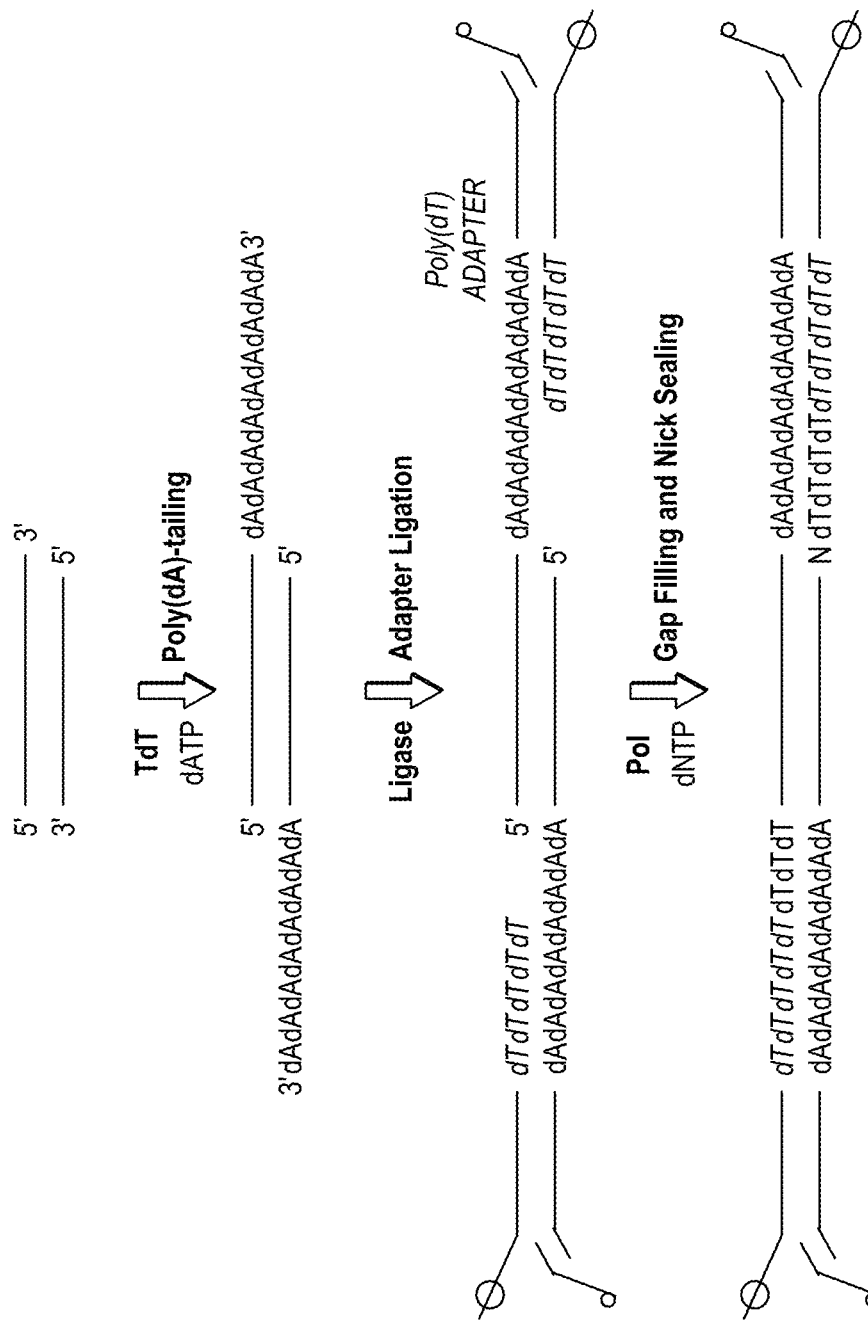
FIG. 22 shows proposed DNA library preparation workflow for ONT sequencing platform. The workflow is comprised of three reactions, poly(dA) tailing catalyzed by terminal deoxynucleotidyl transferase (TdT), ligation of a 3' Poly(dT)-containing adaptor with motor protein (red dot), and gap-filling and nick sealing with DNA polymerase (Pol) and DNA Ligase. Relevant soluble or immobilized enzymes can be utilized to catalyze each enzymatic treatment. Enzymes may be removed, inactivated or present in the final sequencing library.

A new method is proposed here and illustrated in FIG. 22. As shown, the proposed method does not use bead purification and/or may include or exclude use PEG during DNA library preparation. This workflow is comprised of three major enzymatic steps. First, Terminal deoxynucleotidyl transferase (TdT) is employed to catalyze poly(dA) tailing at 3' end of DNA fragments possibly pre-treated with end-polishing enzyme(s). The oligo(dA) overhang can then efficiently ligate with an adaptor with a 3' Poly(dT) overhang and motor protein, in the presence or absence of PEG in the reaction medium. Next, gap-filling and nick sealing can be accomplished with DNA polymerase and DNA Ligase. Enzymes may be removed, inactivated or present in the final sequencing library. Breakage of DNA molecules may be reduced and/or recovery of long DNA templates may be improved by avoiding use of bead purification and/or PEG. As practitioners having the benefit of this disclosure will appreciate, TdT can add other types of oligos, such as poly(dT) or poly(dG) to be suitable for other adaptor ligation strategies in the absence of PEG or DNA-compacting factor. Thus, different enzymes and tailing approaches can be designed to prepare DNA-adaptor molecules anchored with motor protein and other features required for nanopore sequencing.

Example 12: DNA Library Preparation

Figure 23:
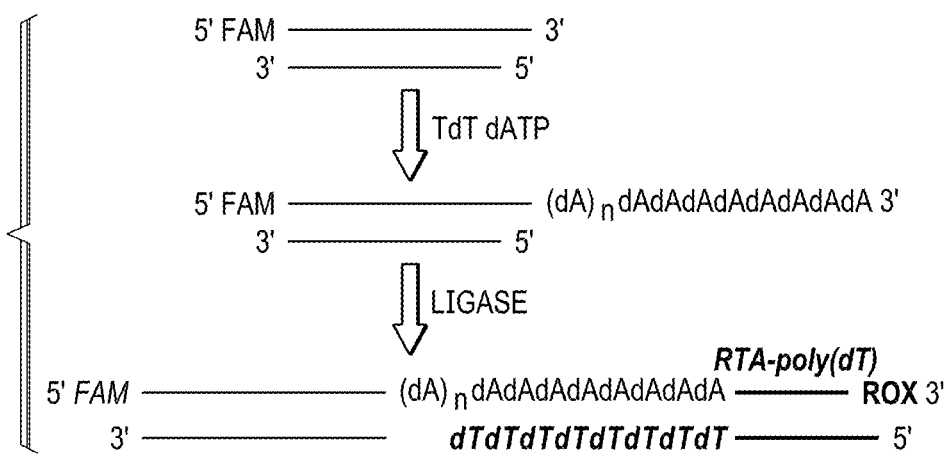
FIG. 23 shows a two-step reaction of poly(dA) tailing of a synthetic double-stranded DNA substrate (possessing a FAM probe) catalyzed by TdT and subsequent ligation with a synthetic adaptor, RTA-poly(dT) possessing a ROX probe.

This example demonstrates poly(dA) tailing of a synthetic DNA substrate and subsequent ligation of the products possessing various lengths of 3' poly(dA) sequences to an adaptor having a 3' poly(dT) overhang as illustrated in FIG. 23.

Example 6A. Poly(dA)-Tailing Mediated by Terminal Deoxynucleotidyl Transferase (TdT)

This example demonstrates poly(dA) tailing of a synthetic DNA substrate by Terminal deoxynucleotidyl Transferase (TdT). A double-stranded DNA substrate was formed by annealing two oligonucleotides, with one possessing a 5' fluorophore probe, FAM and 3' protruding overhang for addition of Poly(dA) tails. 5'FAM-labeled double-stranded DNA was treated with TdT in the presence of various concentrations of dATP to create different substrate to dATP ratios (e.g. 1:100 and 1:200). CE analysis was performed to assess the incorporation of dAMP at the 3' termini of 5'FAM-labeled DNA strand and estimation of the lengths (or range) of poly(dA) tails.

3' poly(dA) tailing was carried out in a 30 µl reaction volume in the presence of 0.1 µM of the DNA substrate, 0.5 µl (20 units) of TdT (NEB, M0315S, 40,000 units/ml,), 1×TdT Reaction Buffer (NEB), 0.25 mM $CoCl_2$ and 10 or 20 µM of dATP. The reactions were performed at 37° C. for 30 min, followed by treatment at 70° C. for 10 min in a T-100 Thermocycler (Bio-Rad Laboratories, Hercules, Calif.). The reactions were terminated by diluting in 1:1 ratio in 50 mM EDTA and 0.1% Tween-20, and analyzed by CE technique and Peak Scanner software. Results shown in FIG. 24A demonstrate that poly(dA) tailing can be performed in 1× TdT buffer supplemented with $CoCl_2$. Efficient conversion of the DNA substrate to poly(dA) tailed products of various lengths was observed after treatment with TdT and the length of the poly(dA) can be modulated by the control of substrtate-to-dATP ratio.

Example 12B. Sequential Poly(dA) Tailing and Adaptor Ligation

The FAM-labeled double-stranded DNA substrate was assayed for sequential poly(dA) tailing with soluble TdT as described in EXAMPLE 12A and adaptor ligation with soluble T4 DNA Ligase.

A modified RTA adaptor, RTA-Poly(dT) was made by annealing two oligonucleotides, derived from the sequences of RTA (provided by ONT), with one oligonucleotide containing 5' phospho group and 3' ROX probe, and the second one being modified to possess 3' poly(dT).3' poly(dA) tailing was carried out in a 30 µl reaction volume in the presence of 0.1 µM of the DNA substrate, 1 unit of Terminal Deoxynucleotide Transferase (NEB, M0315S, 40,000 units/ml,), 1×TdT Reaction Buffer (NEB), 0.25 mM $CoCl_2$ and 10, 20 or 50 µM of dATP. The reactions were performed at 37° C. for 30 mM, followed by treatment at 70° C. for 10 mM in a T-100 Thermocycler (Bio-Rad Laboratories, Hercules, Calif.). Next, adaptor ligation was performed at 25° C. for 30 min after addition of 100 nM RTA-poly(dT), 1 mM ATP and 1 µl of T4 DNA Ligase (NEB, M0202S, 400,000 units/µl) to the TdT-treated samples. The reactions were terminated by diluting in 50 mM EDTA and 0.1% Tween-20, and analyzed by CE technique and Peak Scanner software. Efficient conversion of the DNA substrate to poly(dA) tailed products of various lengths was observed after treatment with TdT. Joining of poly(dA) tailed products and modified RTA was also detected because of the shift of the FAM labeled products and the co-localization of FAM and ROX signals after ligation reaction, in comparison with the TdT-treated sample.

FIG. 24B shows a peak formed by a range of FAM-labeled products (in blue), representing various 3' poly(dA) lengths. Subsequently, the reaction medium containing the poly(dA)-tailed DNA products, was incubated with T4 DNA ligase and RTA-poly(dT) adaptor possessing 3' poly(dT) and 5' ROX. FIG. 24C shows co-localization of the fluorescence signals of FAM (blue) and ROX (red) indicates ligation of the 5'FAM-labeled DNA species to the 3' ROX-labeled strand of the adaptor. Successful ligation also resulted in a shift of the FAM-labeled species (major peak in TdT sample) to higher molecular products (major Peak in TdT/T4 DNA Ligase sample).

Results shown FIG. 24B and FIG. 24C demonstrate that both poly(dA) and ligation reactions can be performed in 1×TdT buffer supplemented with $CoCl_2$.

Example 12C. Ligation of Poly(dA) Tailed DNA with Adaptor with Soluble and Immobilized Ligase As shown in FIG. 25, a FAM-labeled double-stranded DNA substrate was first tailed using soluble TdT as described in EXAMPLE 6A and then ligated to an adapter with either soluble or immobilized T4 DNA Ligase. 3' poly(dA) tailing was carried out in a 30 µl reaction volume in the presence of 0.1 µM of the DNA substrate, 1 unit of Terminal Deoxynucleotide Transferase (NEB, M0315S, 40,000 units/ml,), 1×TdT Reaction Buffer (NEB), 0.25 mM $CoCl_2$ and 10, 20 or 50 µM of dATP. The reactions were performed at 37° C. for 30 mM, followed by treatment at 70° C. for 10 min in a T-100 Thermocycler (Bio-Rad Laboratories, Hercules, Calif.). Next, adaptor ligation was performed at 25° C. for 30 min after addition of 100 nM RTA-poly(dT), 1 mM ATP and 1 µl of T4 DNA Ligase (NEB, M0202S, 400,000 units/µl) or immobilized T4 DNA Ligase (NEB, Production Lot 1, 60 units/µl) to the TdT-treated samples. The reactions were terminated by diluting in 50 mM EDTA and 0.1% Tween-20, and analyzed by CE technique and Peak Scanner software. Efficient conversion of the DNA substrate to poly(dA) tailed products of various lengths was observed after treatment with TdT. Poly(dA) tailed products and modified RTA were detected with either soluble or immobilized T4 DNA ligase because of the shift of the FAM labeled products and the co-localization of FAM and ROX signals after ligation reaction, in comparison with the TdT-treated sample. These results show that both poly (dA) and ligation reactions can be performed in 1×TdT buffer supplemented with $CoCl_2$.

Example 13: DNA Library Construction Using Immobilized DNA Modifying Enzymes

Many existing methods rely on steps (e.g., AMPure® bead purification) that shear long DNA molecules and are detrimental to long-read sequencing. In addition to use for RNA library preparation for sequencing, immobilized enzymes can be used to construct DNA libraries. FIG. 26 shows a schematic of DNA library construction using a set of four immobilized DNA modifying enzymes (IM-T4 DNA polymerase IM-T4 PNK, IM-Taq DNA Pol, IM-T4 DNA Ligase). Soluble forms of these enzymes are currently used for Nanopore DNA library construction. The following example sets forth the use of relevant immobilized enzymes to generate a DNA library by using an oligo DNA model system with a CE technique to conduct step-by-step analyses.

Example 14: DNA Library Construction Using Immobilized DNA Modifying Enzymes

A DNA library construction protocol for nanopore sequencing may include fragmentation, end repair (blunting and 5' phosphorylation), 3' A-tailing and adaptor ligation. Once the sample DNA has been sheared, the fragment ends are repaired by blunting and 5' phosphorylation with a mixture of enzymes, such as T4 polynucleotide kinase (PNK) and T4 DNA polymerase (T4 DNA pol). This end repair step is followed by 3' A-tailing at 37° C. using a mesophilic polymerase such as Klenow Fragment 3'-5' exonuclease minus[11], or at elevated temperatures using a thermophilic polymerase such as Taq DNA polymerase (Taq DNA pol) (Head, S. R. et al. Library construction for next-generation sequencing: overviews and challenges. *BioTechniques* 56, 61-64, 66, 68, passim (2014); Star, B. et al. Palindromic Sequence Artifacts Generated during Next Generation Sequencing Library Preparation from Historic and Ancient DNA. *PLOS ONE* 9, e89676 (2014)). 3' A-tailed DNA fragments are ligated to an adaptor using a T/A ligation method and purified using AMPure® beads prior to nanopore sequencing. Bead-based purification step(s) may result in shearing large DNA which is detrimental to long read sequencing. In addition, T/A ligation efficiency is highly dependent on the presence of crowding agent, such as PEG, however, use of a crowding agent, namely PEG, appears to cause large DNA molecules to compact (Warren M. Mardoum, Stephanie M. Gorczyca, Kathryn E. Regan, Tsai-Chin Wu, and Rae M. Robertson-Anderson. Crowding Induces Entropically-Driven Changes to DNA Dynamics That Depend on Crowder Structure and Ionic Conditions. *Front Phys.* 2018; 6: 53; Heikki Ojal, Gabija Ziedait, Anders E. Wallin, Dennis H. Bamford, Edward Hæggstrom. Optical tweezers reveal force plateau and internal friction in PEG-induced DNA condensation. *European Biophysics Journal*, March 2014, Volume 43, Issue 2-3, pp 71-79). Consequently, the PEG-induced DNA compaction may reduce DNA elution from AMPure® beads, resulting in low library yield of large DNA.

An enzyme immobilization strategy was previously utilized to perform DNA library construction for the sequencing on the Illumina platform (Zhang, Aihua, et al. Solid-phase enzyme catalysis of DNA end repair and 3' A-tailing reduces GC-bias in next-generation sequencing of human genomic DNA. *Scientific reports* 8.1 (2018): 1-11.). The relevant DNA-modifying enzymes were produced as SNAP-tagged fusion proteins and immobilized by covalent conjugation onto magnetic beads functionalized with benzyl guanine ligand (the substrate of SNAP-tag). These immobilized enzymes were successfully applied to Illumina DNA library construction in place their soluble counterparts. One of the major of the major advantages is that the enzymes can be removed without heat treatment or AMPure® bead purification.

This example demonstrates that the same set of enzymes can be used for the current workflow of Nanopore DNA library construction. In this example, each enzymatic reaction step was monitored by fluorescence capillary gel electrophoresis (CE) using a synthetic double stranded DNA end-labeled with a fluorescent probe, FAM. DNA was end-repaired for 30 min at 20° C. using immobilized T4 DNA pol and T4 polynucleotide kinase in a 20 µl reaction in the presence of 1×NEBNext End Repair Buffer II. These end-repair enzymes were pelleted on a magnetic rack and the supernatant was transferred to a new tube for 3' A-tailing with immobilized Taq DNA pol at 37° C. for 30 min. The resulting product was ligated to an adaptor with an end possessing 5' phospho group and 3'T. The reactions were terminated by diluting in 50 mM EDTA and 0.1% Tween-20. The reactions were performed in a T-100 Thermocycler (Bio-Rad Laboratories, Hercules, Calif.) and analyzed by CE technique and Peak Scanner software. A partial ligation of the DNA substrate to the adaptor is shown in FIG. 27, indicating that T/A ligation can be performed in 1×NEBNext End Repair Buffer II without supplement with PEG.

What is claimed is:

1. A method of preparing a library for sequencing, comprising:
    (a) in a coupled reaction, (i) contacting a population of nucleic acid fragments with a tailing enzyme to produce tailed fragments, and (ii) ligating to the tailed fragments a sequencing adapter with a ligase to produce adapter-tagged fragments; and
    (b) separating adapter-tagged fragments from the tailing enzyme and the ligase to produce separated adapter-tagged fragments and, optionally, separated tailing enzyme and/or separated ligase, wherein the tailing enzyme and the ligase are co-immobilized on a single support.

2. A method according to claim 1, wherein the population of nucleic acid fragments comprise ribonucleic acid fragments.

3. A method according to claim 1, wherein the tailing enzyme is immobilized on a magnetic bead.

4. A method according to claim 3, wherein the separating the adapter tagged fragments further comprises subjecting the coupled reaction to a magnetic field.

5. A method according to claim 1, wherein the ligase is immobilized on a magnetic bead.

6. A method according to claim 5, wherein the separating the adapter tagged fragments further comprises subjecting the coupled reaction to a magnetic field.

7. A method according to claim 1, wherein the population of nucleic acid fragments comprise deoxyribonucleic acid fragments.

8. A method according to claim 1, wherein the population of nucleic acid fragments has less than 100 ng of nucleic acids.

9. A method according to claim 1, wherein the population of nucleic acid fragments has less than 10 ng of nucleic acids.

10. A method according to claim 1, further comprising:
    (c) in a second coupled reaction, (i) contacting a second population of nucleic acid fragments with the separated tailing enzyme to produce additional tailed fragments, and (ii) ligating to the additional tailed fragments a second sequencing adapter with the separated ligase to produce additional adapter-tagged fragments, and
    (d) separating the additional adapter-tagged fragments from the separated tailing enzyme and the separated ligase to produce separated additional adapter-tagged fragments, separated tailing enzyme, and separated ligase.

11. A method according to claim 10, further comprising:
    (e) translocating the separated adapter-tagged fragments through one or more transmembrane pores;
    (f) detecting electrical changes as the one or more separated adapter-tagged fragments are translocated through the one or more transmembrane pores in an insulating membrane to produce an electrical signal; and
    (g) analyzing the electrical signal to generate a sequence read.

12. A method according to claim 11, wherein the one or more transmembrane pores retain about 90% of their initial activity after two hours.

13. A method according to claim 11, wherein the one or more transmembrane pores retain about 50% of their initial activity after 8 hours.

14. A method according to claim 11, wherein the one or more transmembrane pores produce at least 900 sequence reads per transmembrane pore.

15. A method according to claim 1, wherein the sequencing adapter is a single stranded adapter comprising:
    a leader sequence; and
    a first sequence and a second sequence, wherein the first and second sequences are complementary to each other and define a hairpin,
wherein the leader sequence is configured to thread into the one or more transmembrane pores.

* * * * *

SEQUENCE LISTING

<160> NUMBER OF SEQ ID NOS: 3

<210> SEQ ID NO 1
<211> LENGTH: 49
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Gene32FAM-fw
<220> FEATURE:
<221> NAME/KEY: misc_feature
<222> LOCATION: (2)..(2)
<223> OTHER INFORMATION: 6-FAMN

<400> SEQUENCE: 1
catggtgatt acgattcttg cccagtatgt caatacatca gtaaaaata                49

<210> SEQ ID NO 2
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Gene32-rv
<220> FEATURE:
<221> NAME/KEY: misc_feature
<222> LOCATION: (1)..(1)
<223> OTHER INFORMATION: p 5Phos

```
<400> SEQUENCE: 2
atttttactg atgtattgac atactgggca agaatcgtaa tcaccatg          48

<210> SEQ ID NO 3
<211> LENGTH: 64
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: p 5Phos
<220> FEATURE:
<221> NAME/KEY: misc_feature
<222> LOCATION: (32)..(32)
<223> OTHER INFORMATION: ideoxyu

<400> SEQUENCE: 3
gatcggaaga gcacacgtct gaactccagt cacactcttt ccctacacga cgctcttccg    60
atct                                                                 64
```